United States Patent
Schendel et al.

(10) Patent No.: US 10,626,159 B2
(45) Date of Patent: Apr. 21, 2020

(54) HIGH AFFINITY T CELL RECEPTOR AND USE THEREOF

(71) Applicant: MAX-DELBRUECK-CENTRUM FUER MOLEKULARE MEDIZIN, Berlin (DE)

(72) Inventors: Dolores Jean Schendel, Munich (DE); Susanne Wilde, Munich (DE); Bernhard Frankenberger, Munich (DE); Wolfgang Uckert, Berlin (DE)

(73) Assignees: MAX-DELBRUECK-CENTRUM FUER MOLEKULARE MEDIZIN, Berlin (DE); Helmholtz Zentrum München Deutsches Forschungszentrum für Gesundheit und Umwelt (GmbH), Neuherberg (DE)

( * ) Notice: Subject to any disclaimer, the term of this patent is extended or adjusted under 35 U.S.C. 154(b) by 82 days.

(21) Appl. No.: 15/822,970

(22) Filed: Nov. 27, 2017

(65) Prior Publication Data

US 2018/0162921 A1   Jun. 14, 2018

Related U.S. Application Data

(62) Division of application No. 14/224,525, filed on Mar. 25, 2014, now Pat. No. 9,862,755, which is a division of application No. 13/130,665, filed as application No. PCT/EP2009/065705 on Nov. 24, 2009, now Pat. No. 8,697,854.

(30) Foreign Application Priority Data

Nov. 24, 2008   (EP) ..................... 08020396

(51) Int. Cl.
  *A61K 35/17*   (2015.01)
  *C12N 15/85*   (2006.01)
  *C07K 14/725*  (2006.01)
  *A61K 38/17*   (2006.01)

(52) U.S. Cl.
  CPC .......... *C07K 14/7051* (2013.01); *A61K 35/17* (2013.01); *A61K 38/1774* (2013.01); *C12N 15/85* (2013.01); *C07K 2319/40* (2013.01)

(58) Field of Classification Search
  CPC ..... C07K 14/7051; C12N 15/09; C12N 15/85
  USPC ...................................................... 530/350
  See application file for complete search history.

(56) References Cited

U.S. PATENT DOCUMENTS

| | | | |
|---|---|---|---|
| 4,415,553 A | 11/1983 | Zhabilov et al. | |
| 4,568,542 A | 2/1986 | Kronenberg | |
| 4,703,004 A | 10/1987 | Hopp et al. | |
| 4,789,658 A | 12/1988 | Yoshimoto et al. | |
| 4,851,341 A | 7/1989 | Hopp et al. | |
| 4,877,611 A | 10/1989 | Cantrell | |
| 5,156,841 A | 10/1992 | Rapp | |
| 5,290,551 A | 3/1994 | Berd | |
| 5,582,831 A | 12/1996 | Shinitzky | |
| 5,906,936 A | 5/1999 | Eshhar et al. | |
| 6,063,375 A | 5/2000 | Gattoni-Celli et al. | |
| 6,077,519 A | 6/2000 | Storkus et al. | |
| 6,143,292 A | 11/2000 | Slavin | |
| 6,458,585 B1 | 10/2002 | Vachula et al. | |
| 6,805,861 B2 | 10/2004 | Stauss | |
| 7,659,084 B2 | 2/2010 | Frentsch et al. | |
| 8,206,701 B2 | 6/2012 | Schendel et al. | |
| 8,486,694 B2 | 7/2013 | Schendel et al. | |
| 8,697,854 B2 * | 4/2014 | Schendel ........... | C07K 14/7051 536/23.5 |
| 9,409,969 B2 | 8/2016 | Schendel et al. | |
| 9,862,755 B2 * | 1/2018 | Schendel ........... | C07K 14/7051 |
| 2002/0090362 A1 | 7/2002 | Stauss | |
| 2002/0123479 A1 | 9/2002 | Song et al. | |
| 2002/0168351 A1 | 11/2002 | Ohno | |
| 2004/0260061 A1 | 12/2004 | Kaltoft | |
| 2005/0175596 A1 | 8/2005 | Schendel et al. | |
| 2010/0158927 A1 * | 6/2010 | Reiter ................ | C07K 16/2833 424/178.1 |
| 2010/0189728 A1 | 7/2010 | Schendel et al. | |
| 2011/0020308 A1 | 1/2011 | Schendel | |
| 2011/0182945 A1 | 7/2011 | Schendel et al. | |
| 2011/0280889 A1 * | 11/2011 | Schendel ........... | C07K 14/7051 424/178.1 |
| 2011/0280894 A1 | 11/2011 | Krackhardt et al. | |
| 2012/0128704 A1 * | 5/2012 | Schendel ........... | C07K 14/7051 424/185.1 |
| 2014/0141026 A1 | 5/2014 | Schendel et al. | |

(Continued)

FOREIGN PATENT DOCUMENTS

| EP | 1275400 B1 | 11/2004 |
|---|---|---|
| EP | 1870418 A1 | 12/2007 |
| EP | 1878744 A1 | 1/2008 |

(Continued)

OTHER PUBLICATIONS

Kobold et al. (J Natl Cancer Inst (2015) 107(1):364-372).*
Zhou et al. (Blood. 2012;120(22):4334-4342).*
Advisory Action corresponding to U.S. Appl. No. 13/027,827 dated Apr. 25, 2013.
Alajez et al., "Therapeutic potential of a tumor-specific, MHC-unrestricted T-cell receptor expressed on effector cells of the innate and the adaptive immune system through bone marrow transduction and immune reconstitution," Blood. 105(12):4583-9 (2005).

(Continued)

*Primary Examiner* — Lynn A Bristol
(74) *Attorney, Agent, or Firm* — Clark & Elbing LLP

(57) ABSTRACT

The present invention is directed to a high affinity T cell receptor (TCR) against a tumor-associated antigen, an isolated nucleic acid molecule encoding the same, a T cell expressing the TCR, and a pharmaceutical composition for use in the treatment of diseases involving malignant cells expressing the tumor-associated antigen.

6 Claims, 9 Drawing Sheets

Specification includes a Sequence Listing.

(56) References Cited

U.S. PATENT DOCUMENTS

| | | | |
|---|---|---|---|
| 2017/0044233 A1* | 2/2017 | Schendel | C07K 14/7051 |
| 2018/0153946 A1* | 6/2018 | Alemany | A61K 35/761 |

FOREIGN PATENT DOCUMENTS

| | | | |
|---|---|---|---|
| WO | WO-1996/004314 A1 | 2/1996 | |
| WO | WO-1997/004802 A1 | 2/1997 | |
| WO | WO-1997/026328 A1 | 7/1997 | |
| WO | WO-1997/032603 A1 | 9/1997 | |
| WO | WO-1997/041210 A1 | 11/1997 | |
| WO | WO-1998/011202 A1 | 3/1998 | |
| WO | WO-1998/033527 A2 | 8/1998 | |
| WO | WO-1998/058956 A2 | 12/1998 | |
| WO | WO-1999/003976 A2 | 1/1999 | |
| WO | WO-00/76537 A2 | 12/2000 | |
| WO | WO-01/036680 A2 | 5/2001 | |
| WO | WO-2002/036790 A2 | 5/2002 | |
| WO | WO-02/074338 A1 | 9/2002 | |
| WO | WO-2004/027428 A1 | 4/2004 | |
| WO | WO-2006/031221 A1 | 3/2006 | |
| WO | WO-2006/065495 A2 | 6/2006 | |
| WO | WO-2007/065957 A2 | 6/2007 | |
| WO | WO-2007/131092 A2 | 11/2007 | |
| WO | WO-2008/039818 A2 | 4/2008 | |
| WO | WO-2008/071701 A1 | 6/2008 | |
| WO | WO-2010/012829 A1 | 2/2010 | |
| WO | WO-2010/058023 A1 | 5/2010 | |

OTHER PUBLICATIONS

Altman et al., "Phenotypic analysis of antigen-specific T lymphocytes," Science. 274(5284):94-6 (1996).
Amrolia et al., "Allorestricted cytotoxic T cells specific for human CD45 show potent antileukemic activity," Blood. 101(3):1007-14 (2003).
Bachmann et al., "Recall proliferation potential of memory CD8+ T cells and antiviral protection," J Immunol. 175(7):4677-85 (2005).
Bargmann et al., "The neu oncogene encodes an epidermal growth factor receptor-related protein," Nature. 319(6050):226-30 (1986).
Becker et al., "Adoptive tumor therapy with T lymphocytes enriched through an IFN-gamma capture assay," Nat Med. 7(10):1159-62 (2001).
Belmares et al., "Structural factors contributing to DM susceptibility of MHC class II/peptide complexes," J Immunol. 169(9):5109-17 (2002).
Bernhard et al., "Adoptive transfer of autologous, HER2-specific, cytotoxic T lymphocytes for the treatment of HER2-overexpressing breast cancer," Cancer Immunol Immunother. 57(2):271-80 (2008).
Bishop et al., "Allogeneic lymphocytes induce tumor regression of advanced metastatic breast cancer," J Clin Oncol. 22(19):3886-92 (2004).
Blaise et al., "Reduced-intensity preparative regimen and allogeneic stem cell transplantation for advanced solid tumors," Blood. 103(2):435-41 (2004).
Boczkowski et al., "Dendritic cells pulsed with RNA are potent antigen-presenting cells in vitro and in vivo," J Exp Med. 184(2):465-72 (1996).
Boczkowski et al., "Induction of tumor immunity and cytotoxic T lymphocyte responses using dendritic cells transfected with messenger RNA amplified from tumor cells," Cancer Res. 60(4):1028-34 (2000).
Britten et al., "Identification of T cell epitopes by the use of rapidly generated mRNA fragments," J Immunol Methods. 299(1-2):165-75 (2005).
Britten et al., "The use of clonal mRNA as an antigenic format for the detection of antigen-specific T lymphocytes in IFN-gamma ELISPOT assays," J Immunol Methods. 287(1-2):125-36 (2004).
Britten et al., "The use of HLA-A*0201-transfected K562 as standard antigen-presenting cells for CD8(+) T lymphocytes in IFN-gamma ELISPOT assays," J Immunol Methods. 259(1-2):95-110 (2002).

Burrows et al., "T cell receptor repertoire for a viral epitope in humans is diversified by tolerance to a background major histocompatibility complex antigen," J Exp Med. 182(6):1703-15 (1995).
Busch et al., "Coordinate regulation of complex T cell populations responding to bacterial infection," Immunity. 8(3):353-62 (1998).
Butterfield et al., "Generation of melanoma-specific cytotoxic T lymphocytes by dendritic cells transduced with a MART-1 adenovirus," J Immunol. 161(10):5607-13 (1998).
Carella et al., "Reduced intensity conditioning for allograft after cytoreductive autograft in metastatic breast cancer," Lancet. 366(9482):318-20 (2005).
Chazin et al., "Transformation mediated by the human HER-2 gene independent of the epidermal growth factor receptor," Oncogene 7(9):1859-66 (1992).
Childs et al., "Regression of metastatic renal-cell carcinoma after nonmyeloablative allogeneic peripheral-blood stem-cell transplantation," N Engl J Med. 343(11):750-8 (2000).
Clay et al., "Efficient transfer of a tumor antigen-reactive TCR to human peripheral blood lymphocytes confers anti-tumor reactivity," J Immunol. 163(1):507-13 (1999).
Cobleigh et al., "Multinational study of the efficacy and safety of humanized anti-HER2 monoclonal antibody in women who have HER2-overexpressing metastatic breast cancer that has progressed after chemotherapy for metastatic disease," J Clin Oncol. 17(9):2639-48 (1999).
Cohen et al., "Enhanced antitumor activity of murine-human hybrid T-cell receptor (TCR) in human lymphocytes is associated with improved pairing and TCR/CD3 stability," Cancer Res. 66(17):8878-86 (2006).
Coussens et al., "Tyrosine kinase receptor with extensive homology to EGF receptor shares chromosomal location with neu oncogene," Science. 230(4730):1132-9 (1985).
Da et al., "Autologous bone marrow mixed with HLA-haploidentical allogeneic marrow transplantation for treatment of patients with malignant blood diseases," Bone Marrow Transplant. 19(2):107-12 (1997).
Dannull et al., "Current status of dendritic cell-based tumor vaccination," Onkologie. 23(6):544-551 (2000).
Dawicki et al., "Expression and function of 4-1BB during CD4 versus CD8 T cell responses in vivo," Eur J Immunol. 34(3):743-51 (2004).
de Witte et al., "Targeting self-antigens through allogeneic TCR gene transfer," Blood. 108(3):870-7 (2006).
Decision to Grant corresponding to European Patent Application No. 06776623.8-1222 / 1910521 dated Sep. 16, 2010.
Ding et al., "Combined transfection with EBV-specific epitopes and HLA-A2 genes is more effective than separate transfection in promoting CTL lysis against nasopharyngeal carcinoma," Cell Mol Immunol. 1(3):229-34 (2004).
Disis et al., "Generation of T-cell immunity to the HER-2/neu protein after active immunization with HER-2/neu peptide-based vaccines," J Clin Oncol. 20(11):2624-32 (2002).
Drexler et al., "Modified vaccinia virus Ankara for delivery of human tyrosinase as melanoma-associated antigen: induction of tyrosinase- and melanoma-specific human leukocyte antigen A*0201-restricted cytotoxic T cells in vitro and in vivo," Cancer Res. 59(19):4955-63 (1999).
Dudley et al., "Adoptive cell transfer therapy following non-myeloablative but lymphodepleting chemotherapy for the treatment of patients with refractory metastatic melanoma," J Clin Oncol. 23(10):2346-57 (2005).
Dudley et al., "Adoptive-cell-transfer therapy for the treatment of patients with cancer," Nat Rev Cancer. 3(9):666-75 (2003).
Dudley et al., "Cancer regression and autoimmunity in patients after clonal repopulation with antitumor lymphocytes," Science. 298(5594):850-4 (2002).
Dupont et al., "Artificial antigen-presenting cells transduced with telomerase efficiently expand epitope-specific, human leukocyte antigen-restricted cytotoxic T cells," Cancer Res. 65(12):5417-27 (2005).
Efferson et al., "Stimulation of human T cells by an influenza A vector expressing a CTL epitope from the HER-2/neu protooncogene results in higher numbers of antigen-specific TCRhi cells than

(56) References Cited

OTHER PUBLICATIONS stimulation with peptide. Divergent roles of IL-2 and IL-15," Anticancer Res. 25(2A):715-24 (2005).
Engels et al., "Redirecting human T lymphocytes toward renal cell carcinoma specificity by retroviral transfer of T cell receptor genes," Hum Gene Ther. 16(7):799-810 (2005).
Engels et al., "Retroviral vectors for high-level transgene expression in T lymphocytes," Hum Gene Ther. 14(12):1155-68 (2003).
European Search Report corresponding to European Patent Application No. 10 179 257.0-1222 dated Oct. 26, 2010.
Falk et al., "Allogeneic MHC class I ligands and their role in positive and negative regulation of human cytotoxic effector cells," Hum Immunol. 63(1):8-19 (2002).
Falk et al., "Expression of HLA-C molecules confers target cell resistance to some non-major histocompatibility complex-restricted T cells in a manner analogous to allospecific natural killer cells," J Exp Med. 182(4):1005-18 (1995).
Falk et al., "Retaliation against tumor cells showing aberrant HLA expression using lymphokine activated killer-derived T cells," Cancer Res. 62(2):480-7 (2002).
Fisk et al., "Identification of an immunodominant peptide of HER-2/neu protooncogene recognized by ovarian tumor-specific cytotoxic T lymphocyte lines," J Exp Med.181(6):2109-17 (1995).
Gao et al., "Allo-major histocompatibility complex-restricted cytotoxic T lymphocytes engraft in bone marrow transplant recipients without causing graft-versus-host disease," Blood. 94(9):2999-3006 (1999).
Gao et al., "Selective elimination of leukemic CD34(+) progenitor cells by cytotoxic T lymphocytes specific for WT1," Blood. 95(7):2198-203 (2000).
Geiger et al., "A generic RNA-pulsed dendritic cell vaccine strategy for renal cell carcinoma," J Transl Med. 3:29 (2005).
Gelder et al., "Six unrelated HLA-DR-matched adults recognize identical CD4+ T cell epitopes from influenza A haemagglutinin that are not simply peptides with high HLA-DR binding affinities," Int Immunol. 10(2):211-22 (1998).
GenBank Accession No. M97708.1, "Human T-cell receptor (V alpha 13.1, J alpha V, C alpha 1) mRNA," <www.ncbi.nlm.nih.gov/nuccore/M97708> retrieved on Apr. 21, 2014 (1 page).
GenBank Accession No. U11794.1, "Pan troglodytes clone ichv29 T-cell receptor alpha chain mRNA, partial cds," <http://www.ncbi.nlm.nih.gov/nuccore/U11794> retrieved on Apr. 21, 2014 (2 pages).
Gilboa et al., "Cancer immunotherapy with mRNA-transfected dendritic cells," Immunol Rev. 199:251-63 (2004).
Goldsby et al., "Immunology," 5th edition, Chapter 7, Part II, W.H. Freeman Company: New York, pp. 172-177 (2002).
Gong et al., "Fusions of human ovarian carcinoma cells with autologous or allogeneic dendritic cells induce antitumor immunity," J Immunol. 165(3):1705-11 (2000).
Goyarts et al., "Point mutations in the beta chain CDR3 can alter the T cell receptor recognition pattern on an MHC class I/peptide complex over a broad interface area," Mol Immunol. 35(10):593-607 (1998).
Greten et al., "Peptide-beta2-microglobulin-MHC fusion molecules bind antigen-specific T cells and can be used for multivalent MHC-IG complexes," J Immunol Methods. 271(1-2):125-35 (2002).
Heemskerk et al., "Redirection of antileukemic reactivity of peripheral T lymphocytes using gene transfer of minor histocompatibility antigen HA-2-specific T-cell receptor complexes expressing a conserved alpha joining region," Blood. 102(10):3530-40 (2003).
Heiser et al., "Human dendritic cells transfected with RNA encoding prostate-specific antigen stimulate prostate-specific CTL responses in vitro," J Immunol. 164(10):5508-14 (2000).
Ho et al., "In vitro methods for generating CD8+ T-cell clones for immunotherapy from the naïve repertoire," J Immunol Methods. 310(1-2):40-52 (2006).
Hoffmann et al., "Adoptive Cellular Therapy," Seminars in Oncology. 27(2):221-233 (2000).
Intent to Grant corresponding to European Patent Application No. 09 760 145.4-2115 dated May 22, 2012.

Interview Summary corresponding to U.S. Appl. No. 13/027,827 dated Apr. 25, 2013.
Janeway et al., "Immunobiology," 5th edition, Chapters 3 & 5, Garland Publishing, pp. 116-117 and 174-176 (2001).
Jantzer et al., "Human renal cell carcinoma antigen-specific CTLs: antigen-driven selection and long-term persistence in vivo," Cancer Res. 58(14):3078-86 (1998).
Javorovic et al., "Inhibitory effect of RNA pool complexity on stimulatory capacity of RNA-pulsed dendritic cells," J Immunother. 31(1):52-62 (2008).
Javorovic et al., "RNA transfer by electroporation into mature dendritic cells leading to reactivation of effector-memory cytotoxic T lymphocytes: a quantitative analysis," Mol Ther. 12(4):734-43 (2005).
Kazansky, "Intrathymic selection: new insight into tumor immunology," Adv Exp Med Biol. 601:133-44 (2007).
Kazatchkine, "Nomenclature for T-cell receptor (TCR) gene segments of the immune system. WHO-IUIS Nomenclature Sub-Committee on TCR Designation," Immunogenetics. 42(6):451-3 (1995).
Kieback et al., "A safeguard eliminates T cell receptor gene-modified autoreactive T cells after adoptive transfer," Proc Natl Acad Sci U S A. 105(2):623-8 (2008).
Knabel et al., "Reversible MHC multimer staining for functional isolation of T-cell populations and effective adoptive transfer," Nat Med. 8(6):631-7 (2002).
Knutson et al., "Clonal diversity of the T-cell population responding to a dominant HLA-A2 epitope of HER-2/neu after active immunization in an ovarian cancer patient," Hum Immunol. 63(7):547-57 (2002).
Knutson et al., "Immunization of cancer patients with a HER-2/neu, HLA-A2 peptide, p. 369-377, results in short-lived peptide-specific immunity," Clin Cancer Res. 8(5):1014-8 (2002).
Kolb et al., "Graft-versus-leukemia effect of donor lymphocyte transfusions in marrow grafted patients," Blood. 86(5):2041-50 (1995).
Kolb et al., "Graft-versus-leukemia reactions in allogeneic chimeras," Blood. 103(3):767-76 (2004).
Krackhardt et al., "Identification of tumor-associated antigens in chronic lymphocytic leukemia by SEREX," Blood. 100(6):2123-31 (2002).
Kufe et al., "Smallpox, polio and now a cancer vaccine?" Nat Med. 6(3):252-3 (2000).
Kugler et al., "Regression of human metastatic renal cell carcinoma after vaccination with tumor cell-dendritic cell hybrids," Nat Med. 6(3):332-6 (2000).
Kugler et al., "Retraction: Regression of human metastatic renal cell carcinoma after vaccination with tumor cell-dendritic cell hybrids," Nat Med. 9(9):1221 (2003).
Latouche et al., "Induction of human cytotoxic T lymphocytes by artificial antigen-presenting cells," Nat Biotechnol. 18(4):405-9 (2000).
Lattrich et al., "Detection of an elevated HER2 expression in MCF-7 breast cancer cells overexpressing estrogen receptor beta1," Oncol Rep. 19(3):811-7 (2008).
Leisegang et al., "Enhanced functionality of T cell receptor-redirected T cells is defined by the transgene cassette," J Mol Med (Berl). 86(5):573-83 (2008).
Levings et al., "Phenotypic and functional differences between human CD4+CD25+ and type 1 regulatory T cells," Curr Top Microbiol Immunol. 293:303-26 (2005).
Liao et al., "Transfection of RNA encoding tumor antigens following maturation of dendritic cells leads to prolonged presentation of antigen and the generation of high-affinity tumor-reactive cytotoxic T lymphocytes," Mol Ther. 9(5):757-64 (2004).
Manning et al., "Alanine scanning mutagenesis of an alphabeta T cell receptor: mapping the energy of antigen recognition," Immunity. 8(4):413-25 (1998).
Margulies, "TCR avidity: ifs not how strong you make it, ifs how you make it strong," Nat Immunol. 2(8):669-70 (2001).
Marzio et al., "CD69 and regulation of the immune function," Immunopharmacol Immunotoxicol. 21(3):565-82 (1999).

(56) References Cited

OTHER PUBLICATIONS

Mittendorf et al., "Evaluation of the HER2/neu-derived peptide GP2 for use in a peptide-based breast cancer vaccine trial," Cancer. 106(11):2309-17 (2006).
Mittendorf et al., "Investigating the combination of trastuzumab and HER2/neu peptide vaccines for the treatment of breast cancer," Ann Surg Oncol. 13(8):1085-98 (2006).
Morgan et al., "Cancer regression in patients after transfer of genetically engineered lymphocytes," Science. 314(5796):126-9 (2006).
Morgan et al., "High efficiency TCR gene transfer into primary human lymphocytes affords avid recognition of melanoma tumor antigen glycoprotein 100 and does not alter the recognition of autologous melanoma antigens," J Immunol. 171(6):3287-95 (2003).
Moris et al., "Cutting edge: characterization of allorestricted and peptide-selective alloreactive T cells using HLA-tetramer selection," J Immunol. 166(8):4818-21 (2001).
Morris et al., "Prospects for immunotherapy of malignant disease" Clin Exp Immunol. 131(1):1-7 (2003).
Murphy et al., "Gene modification strategies to induce tumor immunity," Immunity. 22(4):403-14 (2005).
Mutis et al., "Generation of minor histocompatibility antigen HA-1-specific cytotoxic T cells restricted by nonself HLA molecules: a potential strategy to treat relapsed leukemia after HLA-mismatched stem cell transplantation," Blood. 100(2):547-52 (2002).
Nair et al., "Induction of carcinoembryonic antigen (CEA)-specific cytotoxic T-lymphocyte responses in vitro using autologous dendritic cells loaded with CEA peptide or CEA RNA in patients with metastatic malignancies expressing CEA," Int J Cancer. 82(1):121-4 (1999).
Nair et al., "Induction of primary carcinoembryonic antigen (CEA)-specific cytotoxic T lymphocytes in vitro using human dendritic cells transfected with RNA," Nat Biotechnol. 16(4):364-9 (1998).
Napolitani et al., "Selected Toll-like receptor agonist combinations synergistically trigger a T helper type 1-polarizing program in dendritic cells," Nat Immunol. 6(8):769-76 (2005).
Neudorfer et al., "Reversible HLA multimers (Streptamers) for the isolation of human cytotoxic T lymphocytes functionally active against tumor- and virus-derived antigens," J Immunol Methods. 320(1-2):119-31 (2007).
Notice of Allowance corresponding to U.S. Appl. No. 10/665,111 dated Feb. 21, 2012.
Notice of Allowance corresponding to U.S. Appl. No. 11/990,054 dated Apr. 16, 2013.
Notification Concerning Transmittal of International Preliminary Report on Patentability (Chapter 1 of the Patent Cooperation Treaty) corresponding to International Patent Application No. PCT/EP2009/065705 dated Jun. 3, 2011.
Notification Concerning Transmittal of International Preliminary Report on Patentability (Chapter I of the Patent Cooperation Treaty) corresponding to International Patent Application No. PCT/EP2007/063704 dated Jun. 25, 2009.
Notification Concerning Transmittal of International Preliminary Report on Patentability (Chapter I of the Patent Cooperation Treaty) corresponding to International Patent Application No. PCT/EP2009/059953 dated Feb. 10, 2011.
Notification of Transmittal of International Search Report and the Written Opinion of the International Searching Authority, or the Declaration corresponding to International Patent Application No. PCT/EP2006/007752 dated Jan. 23, 2007.
Notification of Transmittal of International Search Report and the Written Opinion of the International Searching Authority, or the Declaration corresponding to International Patent Application No. PCT/EP2007/063704 dated Mar. 17, 2008.
Notification of Transmittal of International Search Report and the Written Opinion of the International Searching Authority, or the Declaration corresponding to International Patent Application No. PCT/EP2009/059953 dated Nov. 20, 2009.
Notification of Transmittal of the International Preliminary Report on Patentability corresponding to International Patent Application No. PCT/EP2006/007752 dated Sep. 27, 2007.
Notification of Transmittal of the International Search Report and the Written Opinion on the International Searching Authority, or the Declaration corresponding to International Patent Application No. PCT/EP2009/065705 dated Mar. 4, 2010.
Nückel et al., "HLA-G expression is associated with an unfavorable outcome and immunodeficiency in chronic lymphocytic leukemia," Blood. 105(4):1694-8 (2005).
Ochsenreither et al., "Long term presence of a single predominant tyrosinase-specific T-cell clone associated with disease control in a patient with metastatic melanoma," Int J Cancer. 126(10):2497-502 (2010).
Oelke et al., "Technological advances in adoptive immunotherapy," Drugs Today (Barc). 41(1):13-21 (2005).
Official Action corresponding to Chinese Patent Application No. 200980154272 dated Mar. 19, 2013.
Official Action corresponding to European Patent Application No. 09 781 360.4-1404 dated Jun. 19, 2013.
Official Action corresponding to European Patent Application No. 10 179 257.0-1222 dated Feb. 7, 2012.
Official Action corresponding to Japanese Patent Application No. JP 2002-573045 dated Nov. 18, 2008.
Official Action corresponding to Singapore Patent Application No. SG 201103390-9 dated Apr. 18, 2013.
Official Action corresponding to U.S. Appl. No. 10/665,111 dated Aug. 16, 2011.
Official Action corresponding to U.S. Appl. No. 10/665,111 dated Dec. 27, 2006.
Official Action corresponding to U.S. Appl. No. 10/665,111 dated Jan. 21, 2010.
Official Action corresponding to U.S. Appl. No. 10/665,111 dated Jun. 10, 2009.
Official Action corresponding to U.S. Appl. No. 10/665,111 dated Jun. 11, 2008.
Official Action corresponding to U.S. Appl. No. 10/665,111 dated Jun. 28, 2006.
Official Action corresponding to U.S. Appl. No. 10/665,111 dated Nov. 20, 2008.
Official Action corresponding to U.S. Appl. No. 10/665,111 dated Sep. 4, 2007.
Official Action corresponding to U.S. Appl. No. 11/990,054 dated Feb. 26, 2013.
Official Action corresponding to U.S. Appl. No. 11/990,054 dated Jul. 11, 2011.
Official Action corresponding to U.S. Appl. No. 11/990,054 dated May 3, 2012.
Official Action corresponding to U.S. Appl. No. 12/517,995 dated May 3, 2012.
Official Action corresponding to U.S. Appl. No. 13/027,827 dated Mar. 27, 2012.
Official Action corresponding to U.S. Appl. No. 13/027,827 dated Nov. 15, 2012.
Official Action corresponding to U.S. Appl. No. 13/056,827 dated Mar. 29, 2013.
Official Action corresponding to U.S. Appl. No. 13/056,827 dated Nov. 6, 2012.
Palermo et al., "Qualitative difference between the cytotoxic T lymphocyte responses to melanocyte antigens in melanoma and vitiligo," Eur J Immunol. 35(11):3153-62 (2005).
Papanicolaou et al., "Rapid expansion of cytomegalovirus-specific cytotoxic T lymphocytes by artificial antigen-presenting cells expressing a single HLA allele," Blood. 102(7):2498-505 (2003).
Peoples et al., "Breast and ovarian cancer-specific cytotoxic T lymphocytes recognize the same HER2/neu-derived peptide," Proc Natl Acad Sci U S A. 92(2):432-6 (1995).
Peoples et al., "Clinical trial results of a HER2/neu (E75) vaccine to prevent recurrence in high-risk breast cancer patients," J Clin Oncol. 23(30):7536-45 (2005).
Philip et al., "Transgene expression in dendritic cells to induce antigen-specific cytotoxic T cells in healthy donors," Cancer Gene Ther. 5(4):236-46 (1998).

(56) References Cited

OTHER PUBLICATIONS

Pierce et al., "Combinations of affinity-enhancing mutations in a T cell receptor reveal highly nonadditive effects within and between complementarity determining regions and chains," Biochemistry 49(33):7050-9 (2010).
Regn et al., "Ex vivo generation of cytotoxic T lymphocytes specific for one or two distinct viruses for the prophylaxis of patients receiving an allogeneic bone marrow transplant," Bone Marrow Transplant. 27(1):53-64 (2001).
Rivoltini et al., "Quantitative correlation between HLA class I allele expression and recognition of melanoma cells by antigen-specific cytotoxic T lymphocytes," Cancer Res. 55(14):3149-57 (1995).
Rongcun et al., "Identification of new HER2/neu-derived peptide epitopes that can elicit specific CTL against autologous and allogeneic carcinomas and melanomas," J Immunol. 163(2):1037-44 (1999).
Rosenberg et al., "Cancer immunotherapy: moving beyond current vaccines," Nat Med. 10(9):909-15 (2004).
Rossig et al., "Genetic modification of T lymphocytes for adoptive immunotherapy," Mol Ther. 10(1):5-18 (2004).
Roszkowski et al., "CD8-independent tumor cell recognition is a property of the T cell receptor and not the T cell," J Immunol. 170(5):2582-9 (2003).
Roszkowski et al., "Simultaneous generation of CD8+ and CD4+ melanoma-reactive T cells by retroviral-mediated transfer of a single T-cell receptor," Cancer Res. 65(4):1570-6 (2005).
Roth et al., "Analysis of T cell receptor transcripts using the polymerase chain reaction," Biotechniques. 7(7):746-54 (1989).
Rudolph et al., "How TCRs bind MHCs, peptides, and coreceptors," Annu Rev Immunol. 24:419-66 (2006).
Santegoets et al., "In vitro priming of tumor-specific cytotoxic T lymphocytes using allogeneic dendritic cells derived from the human MUTZ-3 cell line," Cancer Immunol Immunother. 55(12):1480-90 (2006).
Savage et al., "A kinetic basis for T cell receptor repertoire selection during an immune response," Immunity. 10(4):485-92 (1999).
Schaft et al., "Generation of an optimized polyvalent monocyte-derived dendritic cell vaccine by transfecting defined RNAs after rather than before maturation," J Immunol. 174(5):3087-97 (2005).
Schendel et al., "Expression of B7.1 (CD80) in a renal cell carcinoma line allows expansion of tumor-associated cytotoxic T lymphocytes in the presence of an alloresponse," Gene Ther. 7(23):2007-14 (2000).
Schendel et al., "Human CD8+ T lymphocytes," Chapter 9.8, Immunology Methods Manual. Academic Press Ltd.: London, pp. 670-690 (1997).
Schendel et al., "Standardization of the Human in vitro Cell-mediated Lympholysis Technique," Tissue Antigens. vol. 13 pp. 112-120 (1979).
Schendel et al., "Tumor-specific lysis of human renal cell carcinomas by tumor-infiltrating lymphocytes. I. HLA-A2-restricted recognition of autologous and allogeneic tumor lines," J Immunol. 151(8):4209-20 (1993).
Scholten et al., "Codon modification of T cell receptors allows enhanced functional expression in transgenic human T cells," Clin Immunol. 119(2):135-45 (2006).
Schuster et al., "Allorestricted T cells with specificity for the FMNL1-derived peptide PP2 have potent antitumor activity against hematologic and other malignancies" Blood. 110(8):2931-9 (2007).
Slamon et al., "Human breast cancer: correlation of relapse and survival with amplification of the HER-2/neu oncogene," Science. 235(4785):177-82 (1987).
Slamon et al., "Use of chemotherapy plus a monoclonal antibody against HER2 for metastatic breast cancer that overexpresses HER2," N Engl J Med. 344(11):783-92 (2001).
Sommermeyer et al., "Designer T cells by T cell receptor replacement," Eur J Immunol. 36(11):3052-9 (2006).
Speck et al., "Treatment of severe aplastic anaemia with antilymphocyte globulin or bone-marrow transplantation," Br Med J (Clin Res Ed). 282(6267):860-3 (1981).

Stanislawski et al., "Circumventing tolerance to a human MDM2-derived tumor antigen by TCR gene transfer," Nat Immunol. 2(10):962-70 (2001).
Stauss, "Immunotherapy with CTLs restricted by nonself MHC," Immunol Today. 20(4):180-3 (1999).
Stedman, "Vaccine", *Stedman's Medical Dictionary 27th Edition*. Lippincott Williams & Wilkins (2000).
Steinle et al., "In vivo expansion of HLA-B35 alloreactive T cells sharing homologous T cell receptors: evidence for maintenance of an oligoclonally dominated allospecificity by persistent stimulation with an autologous MHC/peptide complex," J Exp Med. 181(2):503-13 (1995).
Su et al., "Antigen presenting cells transfected with LMP2a RNA induce CD4+ LMP2a-specific cytotoxic T lymphocytes which kill via a Fas-independent mechanism," Leuk Lymphoma. 43(8):1651-62 (2002).
Su et al., "The generation of LMP2a-specific cytotoxic T lymphocytes for the treatment of patients with Epstein-Barr virus-positive Hodgkin disease," Eur J Immunol. 31(3):947-58 (2001).
Thiel et al., "Structure and diversity of the T-cell receptor alpha chain in rhesus macaque and chimpanzee," Hum Immunol. 43(2):85-94 (1995).
Toes et al., "CD40-CD40Ligand interactions and their role in cytotoxic T lymphocyte priming and anti-tumor immunity," Semin Immunol. 10(6):443-8 (1998).
Vanclée et al., "Graft-versus-tumor effects on murine mammary carcinoma in a model of nonmyeloablative haploidentical stem cell transplantation," Bone Marrow Transplant. 37(11):1043-9 (2006).
Visseren et al., "Affinity, specificity and T-cell-receptor diversity of melanoma-specific CTL generated in vitro against a single tyrosinase epitope," Int J Cancer. 72(6):1122-8 (1997).
Visseren et al., "CTL specific for the tyrosinase autoantigen can be induced from healthy donor blood to lyse melanoma cells," J Immunol. 154(8):3991-8 (1995).
von Geldern et al., "TCR-independent cytokine stimulation induces non-MHC-restricted T cell activity and is negatively regulated by HLA class I," Eur J Immunol. 36(9):2347-58 (2006).
Voss et al., "Targeting p53, hdm2, and CD19: vaccination and immunologic strategies," Bone Marrow Transplant. 25(Suppl 2):S43-5 (2000).
Wheeler, Salud publica de Mexico. 39(4):283-287 (1997) (abstract).
Wilde et al., "High-quality and high-avidity T cell clones specific for tumor-associated antigens and how to find them," Oncoimmunology. 1(9):1643-44 (2012).
Wilde et al., "Human antitumor CD8+ T cells producing Th1 polycytokines show superior antigen sensitivity and tumor recognition," J Immunol. 189(2):598-605 (2012).
Wölfel et al., "Analysis of antigens recognized on human melanoma cells by A2-restricted cytolytic T lymphocytes (CTL)," Int J Cancer. 55(2):237-44 (1993).
Wölfl et al., "Quantitation of MHC tetramer-positive cells from whole blood: evaluation of a single-platform, six-parameter flow cytometric method," Cytometry A. 57(2):120-30 (2004).
Xue et al., "Elimination of human leukemia cells in NOD/SCID mice by WT1-TCR gene-transduced human T cells," Blood. 106(9):3062-7 (2005).
Xue et al., "Exploiting T cell receptor genes for cancer immunotherapy," Clin Exp Immunol. 139(2):167-72 (2005).
Yee et al., "Isolation of high avidity melanoma-reactive CTL from heterogeneous populations using peptide-MHC tetramers," J Immunol. 162(4):2227-34 (1999).
Zaks et al., "Immunization with a peptide epitope (p. 369-377) from HER-2/neu leads to peptide-specific cytotoxic T lymphocytes that fail to recognize HER-2/neu+ tumors," Cancer Res 58(21):4902-8 (1998).
Zhao et al., "High-efficiency transfection of primary human and mouse T lymphocytes using RNA electroporation," Mol Ther. 13(1):151-9 (2006).
Zhao et al., "Primary human lymphocytes transduced with NY-ESO-1 antigen-specific TCR genes recognize and kill diverse human tumor cell lines," J Immunol. 174(7):4415-23 (2005).

(56) References Cited

OTHER PUBLICATIONS

Zhou et al., "High throughput analysis of TCR-beta rearrangement and gene expression in single T cells," Lab Invest. 86(3):314-21 (2006).

* cited by examiner

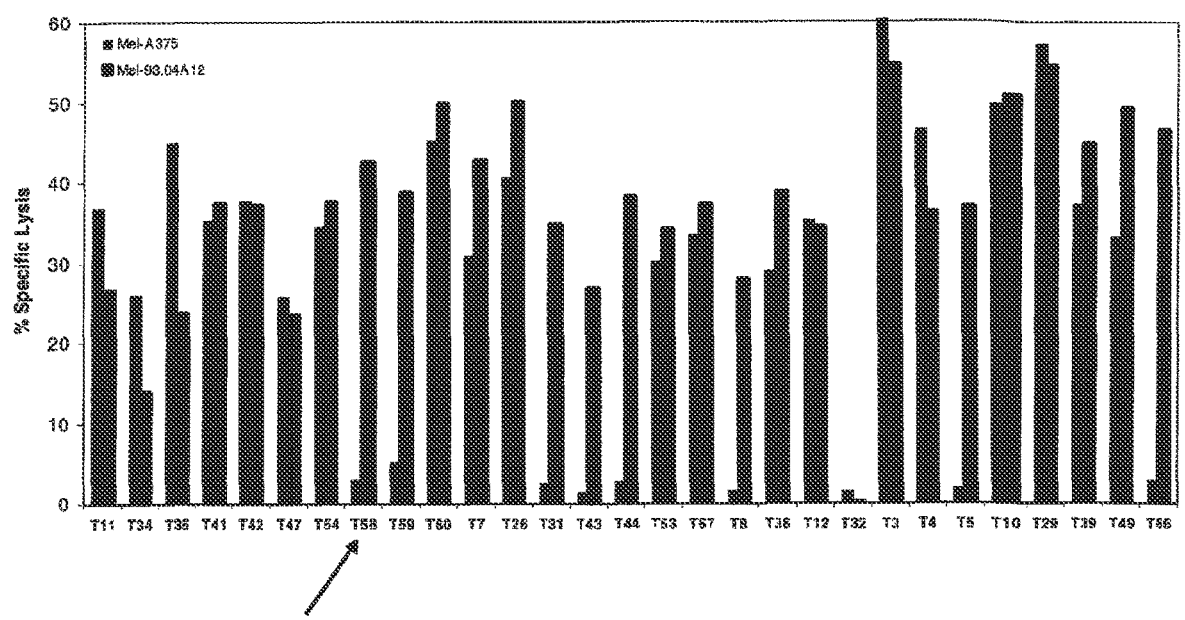
Fig. 1 : Initial screen for tyrosinase-peptide specific T cells
Specificity: HLA-A2 + tyrosinase-peptide YMDGTMSQV Figs. 2A-2D : Allo-restricted T cell clone T58 vs.
patient derived T cell clone IVS-B
Specificity: HLA-A2 + tyrosinase-peptide YMDGTMSQV Figs. 3A-3C : Allo-restricted T cell clone T58 vs.
patient derived T cell clone IVS-B
Recognition of primary tumor cells Figs. 4A-4D : TCR-T58 transduced PBL
Specificity: HLA-A2 + tyrosinase-peptide YMDGTMSQV Figs. 5A-5B : TCR-IVS-B vs. TCR-T58 transduced PBL
Specificity: HLA-A2 + tyrosinase-peptide YMDGTMSQV

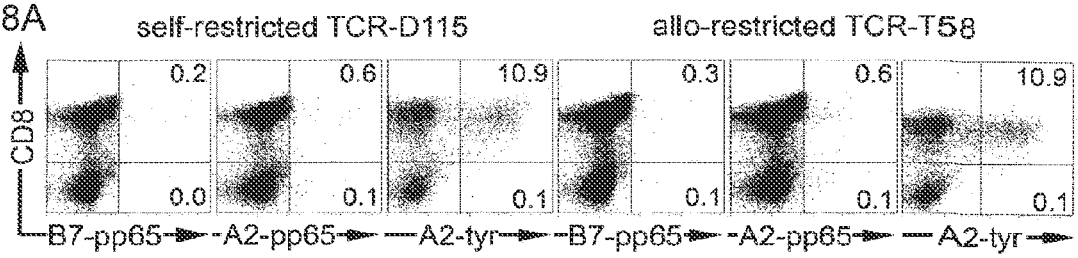
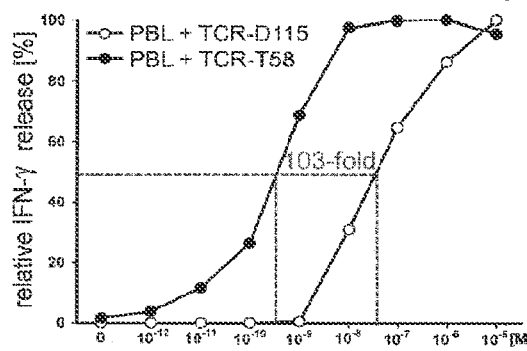
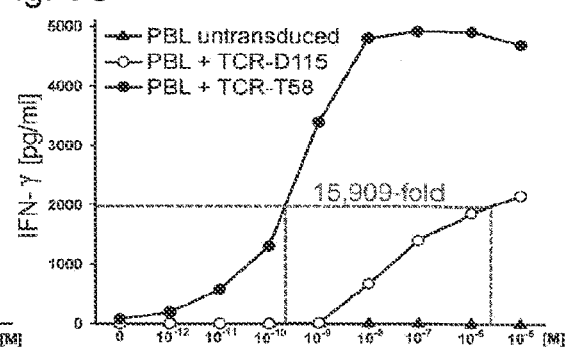
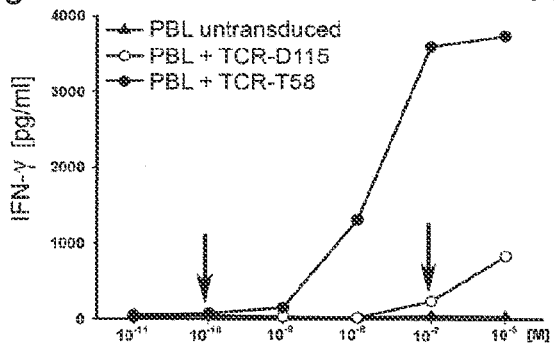
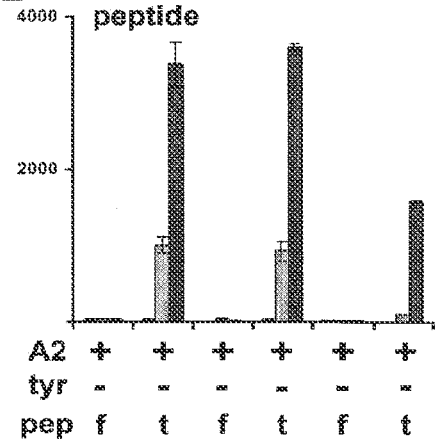
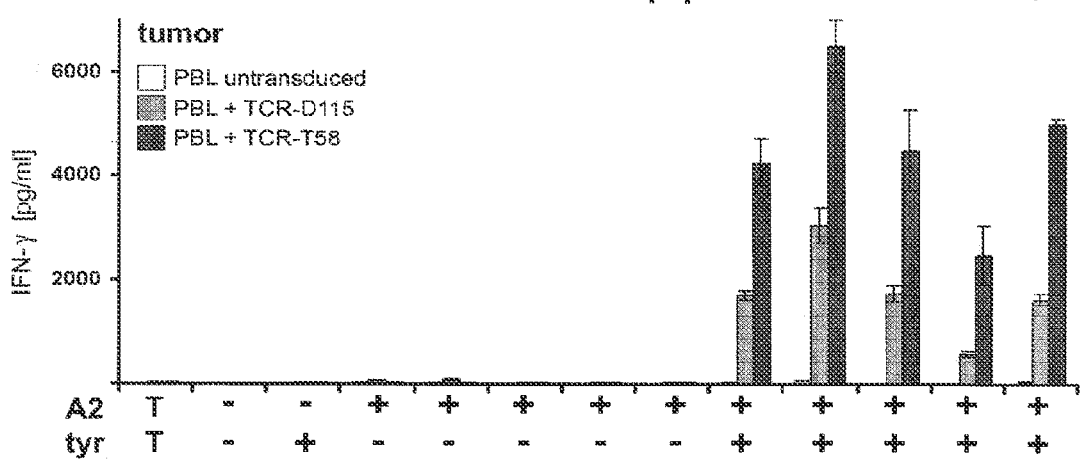

HIGH AFFINITY T CELL RECEPTOR AND USE THEREOF

CROSS REFERENCE TO RELATED APPLICATIONS

This application is a divisional of U.S. patent application Ser. No. 14/224,525, filed Mar. 25, 2014 (now U.S. Pat. No. 9,862,755), which is a divisional of U.S. patent application Ser. No. 13/130,665; filed May 23, 2011 (now U.S. Pat. No. 8,697,854); which itself is a National Stage Entry of PCT International Patent Application Serial No. PCT/EP2009/065705, filed Nov. 24, 2009; which itself claims the benefit of European Patent Application Serial No. EP 08020396.1, filed Nov. 24, 2008. The disclosure of each of these applications is incorporated herein by reference in its entirety.

FIELD OF THE INVENTION

The present invention is directed to a high affinity T cell receptor (TCR) against a tumor-associated antigen, an isolated nucleic acid molecule encoding same, a T cell expressing said TCR, and a pharmaceutical composition for use in the treatment of diseases involving malignant cells expressing said tumor-associated antigen.

BACKGROUND OF THE INVENTION

TCR's are members of the immunoglobulin superfamily and usually consist of two subunits, namely the α- and β-subunits. These possess one N-terminal immunoglobulin (Ig)-variable (V) domain, one Ig-constant (C) domain, a transmembrane/cell membrane-spanning region, and a short cytoplasmic tail at the C-terminal end. The variable domains of both the TCR α-chain and β-chain have three hypervariable or complementarity determining regions (CDRs), whereas the variable region of the β-chain has an additional area of hypervariability (HV4) that does not normally contact antigen and therefore is not considered a CDR.

CDR3 is the main CDR responsible for recognizing processed antigen, although CDR1 of the alpha chain has also been shown to interact with the N-terminal part of the antigenic peptide, whereas CDR1 of the β-chain interacts with the C-terminal part of the peptide. CDR2 is thought to recognize the MHC. CDR4 of the β-chain is not thought to participate in antigen recognition, but has been shown to interact with superantigens. The constant domain of the TCR domain consists of short connecting sequences in which a cysteine residue forms disulfide bonds, which forms a link between the two chains.

The affinity of TCR's for a specific antigen makes them valuable for several therapeutic approaches. For example, cancer patients, such as melanoma patients, can be effectively treated by using adoptive immunotherapy.

The adoptive transfer of lymphocytes in the setting of allogeneic stem cell transplantation (SCT) has demonstrated the power of the immune system for eradicating hematological malignancies (Kolb et al. 1995). It appears that SCT can also function to eliminate solid tumors, such as renal cell carcinomas (RCC) in some cases (reviewed in Kolb et al. 2004 and Dudley and Rosenberg, 2003). In SCT recipients, the elimination of malignant cells may only occur after several months up to a year, due to the fact that specific T cells must be activated in vivo and must then expand to adequate numbers following the development of the new hematopoietic system in the transplant recipient. Alternatively, after a period of time (approximately 60 days) during which tolerance is established in the SCT recipient, a transfer of unprimed, unseparated lymphocytes can be made to speed up the generation of immune responses directed against tumor cells. Here again, the specific lymphocytes capable of attacking tumor cells must be activated and expanded from the low frequency precursor lymphocytes that are present among the unselected population of lymphocytes that are transferred. Donor lymphocyte infusions (DLI) of unselected lymphocyte populations after SCT work well for the elimination of chronic myelogenous leukemia (CML), which grows slowly, but are less effective in the eradication of acute leukemia, partly due to the fact that the growth of the malignant cells outpaces the expansion capacity of the immune cells. This same expansion differential in which immune cells expand more slowly than tumor cells, also impacts on the poor immune elimination of rapidly progressing solid tumors. A second handicap in the use of unselected mixed lymphocyte populations in DLI is that T cells may also be transferred that have the capacity to attack normal cells and tissues of the recipient, leading to graft-versus-host-disease (GVHD), a disease with high morbidity and mortality.

Recent studies have demonstrated that the adoptive transfer of selected T cells with defined peptide specificities can lead to major reductions in tumor burden in an autologous setting, particularly if patients have been pretreated with non-myeloablative regimens (Dudley et al. 2002, 2003). This eliminates the need to perform SCT in the tumor patient, and thereby also bypasses the problem of GVHD.

In order to extend the capacity to use adoptive cell therapy (ACT) to treat patients with more rapidly growing tumors, it is a goal to transfer enriched, peptide-specific effector T cells (both CD4 T helper cells and cytotoxic T lymphocytes) that have been selected for their ligand specificities to effectively attack tumor cells while avoiding serious attack of normal tissues. These cells are to be rapidly expanded to large numbers ex vivo and then used for ACT. Alternatively, the T cell receptors (TCR) of such ligand-specific T cells can be cloned and expressed as TCR-transgenes in activated lymphocytes, using either recipient peripheral blood lymphocytes or activated T cell clones with defined specificities that grow well and do not have the capacity to attack normal host tissues.

As examples, an expanded allospecific T cell clone that is specific for an MHC molecule not expressed by the recipient or an expanded T cell clone specific for a virus, such as cytomegalovirus or Epstein-Barr virus, could be used as recipient cells for the transgenic TCR. The availability of a panel of transgenic TCR vectors, recognizing different MHC-peptide ligands could be used to develop large numbers of pre-activated T cells of both the CD4 and CD8 subtypes, thereby allowing large numbers of effector lymphocytes to be rapidly prepared and transferred to patients whose tumors express the corresponding TCR ligands. This would save time in achieving the numbers of specific T cells required to control tumor growth, possibly leading to more effective tumor eradication of rapidly progressing tumors.

Because the determinants that specific T cells recognize on leukemia and lymphomas, as well as solid tumor cells, often represent self-peptides derived from over-expressed proteins that are presented by self-MHC molecules, the affinity of their T cell receptors (TCR) is low, since T cells bearing high affinity receptors have been eliminated through the process of negative selection which is applied to lymphocytes during their development in the thymus to prevent autoimmunity. More effective tumor cell recognition occurs if the T cells are generated from lymphocyte populations that have not been negatively selected against self-MHC-molecules during their development in the thymus.

WO 2006/031221 pertains to T cell receptors against tumor-associated antigens, nucleic acids encoding the same, vectors and cells comprising the nucleic acids encoding the T cell receptors, and methods of use thereof. Among others, it is disclosed that the TCR subunits have the ability to form TCR that confer specificity to T cells for tumor cells presenting MART-I, NY-ESO-I, and melanoma-related gp100.

In the prior art, several scientific and patent documents are existing, which describe TCR, which are able to recognise and bind tyrosinase. Visseren et al. (Int. J. Cancer (1997) 72, 1122-1128) describe the affinity and specificity of several tyrosinase-specific TCR and suggest to use these TCR as a specific treatment of melanoma patients.

Roszkowski et al. (J. Immunol. (2003) 170, 2582-2589 and Cancer Res. (2005) 65, 1570-1576) the like are characterising tyrosinase-specific TCR.

U.S. Pat. No. 5,906,936 is directed to cytotoxic T-cells which kill non-MHC-restricted target cells and not to cells, which comprise specific TCR sequences.

WO97/32603 is directed to a method for producing non-human TCR and TCR specific for human HLA-restricted tumor antigens. Furthermore, the TCR-nucleic acids and recombinant T-cells are described as well as the administration of TCR recombinant T-cells for the treatment of several diseases.

WO2007/065957 describes an effector T-cell transfected with an antigen specific TCR coding RNA wherein the transfected T-cell recognizes the antigen in a complex with the MHC-molecule and binds the same. As a potential tumor antigen, MART-1 (Melan-A), tyrosinase and survivin are named.

WO2008/039818 discloses MART-1 and tyrosinase-specific TCR sequences and describes the enhancement of antigen recognition by substitution in the CDR2 region.

The above prior art TCR sequences are all derived from autologous or xenogeneic, but not allogeneic, sources.

For example, TCR sequences are from peripheral blood or from tumor infiltrating lymphocytes of HLA-A2 positive melanoma patients. This means that all these TCR are HLA-A2 self-restricted TCRs, or, are HLA-DP4 restricted, NY-ESO-1 specific, both derived from autologous sources. As an alternative, as disclosed in WO97/32603, the TCR is derived from an HLA-A2 transgenic mouse, so in this case the sequence is xenogeneic.

However, the available prior art documents do not show TCR sequences, which are allo-restricted and tyrosinase-specific.

Thus, there is still an important need to find means to generate T cells that bear TCR with high functional avidity that have the capacity to recognize specific ligands on tumor cells. Although adoptive transfer of T cells expressing transgenic T cell receptors (TCR) with anti-tumor function is a hopeful new therapy for patients with advanced tumors, there is a critical bottleneck in identifying high-avidity T cells with TCR specificities needed to treat different malignancies.

SUMMARY OF THE INVENTION

Therefore, it is an object of the present invention to provide TCR or functional parts thereof, such as CDR3 regions, which show high affinity against tumor-associated antigens, in particular tyrosinase. It is a further object of the invention to provide pharmaceutical compositions for use in adoptive cell therapy which allow an effective treatment of diseases involving malignant cells expressing tyrosinase, preferably melanomas, gliomas, glioblastomas, and/or rare tumors of ectodermal origin.

These objects are solved by the subject-matter of the independent claims. Preferred embodiments are indicated in the dependent claims.

TCR specific for the melanoma-associated antigen, tyrosinase, could be isolated by the inventors and it could be shown that TCR derived from the allo-restricted clone were superior in recognition of specific peptide and tumor cells after expression as transgenes in recipient lymphocytes. Therefore, TCR's and functional parts thereof, such as CDR3 regions could be identified, which find application in adoptive cell therapy for the treatment of several malignancies.

A number of T cell clones with specificity for various tumor-associated antigens have been reported over the years (see above). Most of these TCR are restricted by self-MHC molecules. The TCR sequences disclosed herein, however, are allo-restricted and show high-avidity in recognition of their specific ligands. The TCR of the present invention are not self-MHC-restricted and therefore have higher structural affinity for interactions with MHC-peptide ligands that target tumor cells via common over-expressed self proteins. As it will be outlined in the EXAMPLES, the TCR of the present invention were derived from a T cell clone generated by priming CD8* T cells with autologous dendritic cells from an HLA-A2 negative donor co-expressing allogeneic HLA-*A0201 molecules and an antigen. As a result, the present TCR are of therapeutic use for the treatment of HLA-A2 positive patients.

In more detail, T cell responses against tumors are often directed against self-MHC molecules presenting peptides derived from over-expressed self-proteins. In general, T cells with high avidity for self-peptide/self-MHC ligands are eliminated by negative selection to prevent autoimmunity. The TCR affinity of remaining T cells specific for self-ligands is normally low, however high-avidity T cells are needed to effectively eradicate tumors. Because negative selection is limited to self-MHC molecules, T cells that recognize allogeneic MHC molecules have not undergone negative selection. However, as described in the present invention if peptides are presented by allogeneic MHC molecules, it is feasible to obtain high-avidity T cells specific for common tumor-associated ligands derived from over-expressed self-proteins.

DETAILED DESCRIPTION OF THE INVENTION

According to a first aspect, the present invention provides a nucleic acid molecule coding for the V(D)J regions of a TCR that recognizes a tumor antigen and comprising the nucleic acid sequence of SEQ ID NO: 1 coding for the α-chain and/or comprising the nucleic acid sequence of SEQ ID NO: 2 coding for the β-chain of said TCR.

Therefore, a TCR of the present invention and a nucleic acid sequence encoding the same may comprise only one of the α-chain or β-chain sequences as defined herein (in combination with a further α-chain or β-chain, respectively) or may comprise both chains.

The term "nucleic acid" as used herein with reference to nucleic acids refers to a naturally-occurring nucleic acid that is not immediately contiguous with both of the sequences with which it is immediately contiguous (one on the 5' end and one on the 3' end) in the naturally-occurring genome of the cell from which it is derived. For example, a nucleic acid can be, without limitation, a recombinant DNA molecule of any length, provided one of the nucleic acid sequences normally found immediately flanking that recombinant DNA molecule in a naturally-occurring genome is removed or absent. Thus, a nucleic acid includes, without limitation, a recombinant DNA that exists as a separate molecule (e.g., a cDNA or a genomic DNA fragment produced by PCR or restriction endonuclease treatment) independent of other sequences as well as recombinant DNA that is incorporated into a vector, an autonomously replicating plasmid, a virus (e.g., a retrovirus, or adenovirus). In addition, an isolated nucleic acid can include a recombinant DNA molecule that is part of a hybrid or fusion nucleic acid sequence.

Furthermore, the term "nucleic acid" as used herein also includes artificially produced DNA or RNA sequences, such as those sequences generated by DNA synthesis based on in silico information.

The nucleic acids of the invention can comprise natural nucleotides, modified nucleotides, analogs of nucleotides, or mixtures of the foregoing as long as they are capable of causing the expression of a polypeptide in vitro, and preferably, in a T cell. The nucleic acids of the invention are preferably RNA, and more preferably DNA.

Furthermore, the present invention also comprises derivatives of the above described nucleic acid molecules, wherein, related to the above SEQ ID NO: 1 and 2, the sequence has been altered by additions, deletions and/or substitutions and wherein the tumor antigen recognizing characteristics are maintained or improved. In other words, the tumor antigen recognizing characteristics are at least maintained.

More precisely, such a derivative is coding for the α- or β-chain, wherein the chain has been altered by one or more additions or deletions of from 1-15 amino acids, the additions or deletions being outside the CDR3 region of each chain, and/or by conservative substitutions of from 1-15 amino acids. It is noted in this connection that also the CDR3 region may be altered, but to a lesser extent. The definition of those amendments is indicated below for the derivatives of fragments coding for the CDR3 region.

Useful changes in the overall nucleic acid sequence in particular are related to codon optimization and the addition of epitope tags, which will be explained in detail below. Such codon optimization can include optimization of expression levels, optimization of avidity for target cells, or both.

In general, it should, however, be noted that the alterations should not diminish or alter the ability of the encoded polypeptide to form part of a TCR that recognizes tumor associated antigens in the context of an MHC, but should facilitate destruction of a cancer cell, and preferably facilitate the regression of a tumor, or other cancerous state.

For example, alterations can be made which lead to conservative substitutions within the expressed amino acid sequence. These variations can be made in complementarity determining and non-complementarity determining regions of the amino acid sequence of the TCR chain that do not affect function. However, as noted above, additions and deletions should not be performed in the CDR3 region (for example an addition of epitope tags).

The concept of "conservative amino acid substitutions" is understood by the skilled artisan, and preferably means that codons encoding positively-charged residues (H, K, and R) are substituted with codons encoding positively-charged residues, codons encoding negatively-charged residues (D and E) are substituted with codons encoding negatively-charged residues, codons encoding neutral polar residues (C, G, N, Q, S, T, and Y) are substituted with codons encoding neutral polar residues, and codons encoding neutral non-polar residues (A, F, I, L, M, P, V, and W) are substituted with codons encoding neutral non-polar residues. These variations can spontaneously occur, be introduced by random mutagenesis, or can be introduced by directed mutagenesis. Those changes can be made without destroying the essential characteristics of these polypeptides, which are to recognize antitumor antigens in the context of an MHC with high avidity so as to enable the destruction of cancer cells. The ordinarily skilled artisan can readily and routinely screen variant amino acids and/or the nucleic acids encoding them to determine if these variations substantially lessen or destroy the ligand binding capacity by methods known in the art.

In a further embodiment, the present invention provides fragments of the above nucleic acid molecules, coding for a CDR3 region of a TCR recognizing a tumor antigen and having the nucleic acid sequence of SEQ ID NO: 3 or 4 or coding for the amino acid sequences of SEQ ID NO: 5 or 6. Alterations in the CDR3 region will be performed according to the considerations described below.

The invention further provides derivatives wherein the CDR3 region has been altered by one or more additions and/or deletions of an overall number of from 1-5 amino acids, but not more than 1-3 contiguous amino acids and/or conservative substitutions of from 1-6 amino acids and wherein the tumor antigen recognizing characteristics are maintained or improved.

This means, more precisely, that additions or deletions may be performed to an extent that 1-5 amino acids are added or deleted in the CDR3 region. If more then one addition or deletion is performed, the overall number of added or deleted amino acids may not exceed 5 amino acids. Further, one single addition or deletion at one site may only be in the range of 1-3 amino acids, i.e. 1-3 contiguous amino acids, since the ligand binding capacity might be deteriorated by performing larger additions/deletions.

A preferred derivative of the nucleic acid molecule encoding the α- or β-chain of said TCR is one, wherein the original sequence of SEQ ID NO: 1 and 2 has been altered by codon optimization. A preferred example of such a derivative coding for the V(D)J regions of a TCR that recognizes a tumor antigen is the nucleic acid sequence of SEQ ID NO: 7 coding for the α-chain and the nucleic acid sequence of SEQ ID NO: 8 coding for the β-chain of said TCR.

Codon optimization is a generic technique to achieve optimal expression of a foreign gene in a cell system. Selection of optimum codons depends on codon usage of the host genome and the presence of several desirable and undesirable sequence motifs. It is noted that codon optimization will not lead to an altered amino acid sequence and, thus, will not fall under the definition of a conservative substitution as contained in this application.

In a preferred embodiment, the tumor antigen is tyrosinase. Tyrosinase expressing malignancies still have a high incidence, for example, around 160,000 new cases of melanoma are diagnosed worldwide each year. According to a report issued by WHO, about 48,000 melanoma related deaths occur worldwide per year. Thus, tyrosinase is a suitable tumor antigen which can serve as a target for tumor treatment.

In a second aspect, the present invention is directed to a TCR, preferably a soluble TCR, encoded by a nucleic acid molecule as defined above or comprising the amino acid sequences of SEQ ID NO: 5 and/or 6.

Said TCR preferably is present in the form of a functional TCR α- and/or β-chain fusion protein, comprising:
a) at least one epitope-tag, and
b) the amino acid sequence of an α and/or β chain of a TCR as defined above or encoded by a nucleic acid molecule as outlined above,
wherein said epitope-tag is selected from
  i) an epitope-tag added to the N- and/or C-terminus of said α- and/or β-chain, or added into the α- and/or β-chain sequence, but outside the CDR3 region,
  ii) an epitope-tag inserted into a constant region of said α- and/or β-chain, and
  iii) an epitope-tag replacing a number of amino acids in a constant region of said α- and/or β-chain.

Epitope tags are short stretches of amino acids to which a specific antibody can be raised, which in some embodiments allows one to specifically identify and track the tagged protein that has been added to a living organism or to cultured cells. Detection of the tagged molecule can be achieved using a number of different techniques. Examples of such techniques include: immunohistochemistry, immunoprecipitation, flow cytometry, immunofluorescence microscopy, ELISA, immunoblotting ("Western"), and affinity chromatography. Epitope tags add a known epitope (antibody binding site) on the subject protein, to provide binding of a known and often high-affinity antibody, and thereby allowing one to specifically identify and track the tagged protein that has been added to a living organism or to cultured cells.

In the context of the present invention, a "functional" T-cell receptor (TCR) α- and/or β-chain fusion protein shall mean an α- and/or β-chain fusion protein that, although the chain includes the epitope-tag and/or has a tag attached to it, maintains at least substantial fusion protein biological activity in the fusion. In the case of the α- and/or β-chain of a TCR, this shall mean that both chains remain able to form a T-cell receptor (either with a non-modified α- and/or β-chain or with another inventive fusion protein α- and/or β-chain) which exerts its biological function, in particular binding to the specific peptide-MHC complex of said TCR, and/or functional signal transduction upon peptide activation.

Preferred is a functional T-cell receptor (TCR) α- and/or β-chain fusion protein according to the present invention, wherein said epitope-tag has a length of between 6 to 15 amino acids, preferably 9 to 11 amino acids.

Even more preferred is a functional T-cell receptor (TCR) α- and/or β-chain fusion protein according to the present invention, wherein said T-cell receptor (TCR) α- and/or β-chain fusion protein comprises two or more epitope-tags, either spaced apart or directly in tandem. Embodiments of the fusion protein can contain 2, 3, 4, 5 or even more epitope-tags, as long as the fusion protein maintains its biological activity/activities ("functional").

Preferred is a functional T-cell receptor (TCR) α- and/or β-chain fusion protein according to the present invention, wherein said epitope-tag is selected from, but not limited to, CD20 or Her2/neu tags, or other conventional tags such as a myc-tag, FLAG-tag, T7-tag, HA (hemagglutinin)-tag, His-tag, S-tag, GST-tag, or GFP-tag. myc, T7, GST, GFP tags are epitopes derived from existing molecules. In contrast, FLAG is a synthetic epitope tag designed for high antigenicity (see, e.g., U.S. Pat. Nos. 4,703,004 and 4,851,341). The myc tag can preferably be used because high quality reagents are available to be used for its detection. Epitope tags can of course have one or more additional functions, beyond recognition by an antibody. The sequences of these tags are described in the literature and well known to the person of skill in art.

In the functional T-cell receptor (TCR) α- and/or β-chain fusion protein according to the present invention, said fusion protein may be for example selected from two myc-tag sequences that are attached to the N-terminus of an α-TCR-chain and/or 10 amino acids of a protruding loop region in the β-chain constant domain being exchanged for the sequence of two myc-tags.

In an embodiment of the present invention, the inventors inserted an amino acid sequence that corresponds to a part of the myc protein (myc-tag) at several reasonable sites into the structure of a T cell receptor and transduced this modified receptor into T cells (see EXAMPLES below). By introducing a tag into the TCR structure, it is possible to deplete the modified cells by administering the tag-specific antibody to the patient.

Those functional TCR fusion proteins may be used in a method for selecting a host cell population expressing a fusion protein selected from the group consisting of a fusion protein comprising a) at least one epitope-providing amino acid sequence (epitope-tag), and b) the amino acid sequence of an α- and/or β-chain of a TCR as defined above, wherein said epitope-tag is selected from an epitope-tag added to the N- and/or C-terminus of said α- and/or β-chain or added into the α- and/or β-chain sequence, but outside the CDR3 region, an epitope-tag inserted into a constant region of said α- and/or β-chain, and an epitope-tag replacing a number of amino acids in a constant region of said α- and/or β-chain; and a TCR comprising at least one fusion protein as above on the surface of the host cell; comprising contacting host cells in a sample with a binding agent that immunologically binds to the epitope-tag, and selection of said host cells based on said binding.

The present invention further provides an immunoglobulin molecule, anticaline, TCR γ/δ chain having a CDR3 region as defined herein (or a derivative thereof) inserted.

In a third aspect, the invention is directed to a T cell expressing a TCR as defined herein or a TCR comprising one of the CDR3 regions as defined above.

Furthermore, the invention provides a vector, preferably a plasmid, shuttle vector, phagemide, cosmid, expression vector, retroviral vector, adenoviral vector or particle and/or vector to be used in gene therapy, which comprises one or more of the nucleic acids as disclosed above.

In the context of the present invention, a "vector" shall mean a nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known to those of ordinary skill in the art. A vector preferably is an expression vector that includes a nucleic acid according to the present invention operably linked to sequences allowing for the expression of said nucleic acid.

A fourth aspect provides a cell, preferably a peripheral blood lymphocyte (PBL) which has been transformed with the above vector. The step of cloning the T cell receptor (TCR) of the isolated T cells and/or expressing the TCR transgenes in PBMC can be done according to established methods such as those described in Engels et al., 2005.

In a fifth aspect, the present invention provides a pharmaceutical composition which comprises a TCR, a T cell or cell (PBL) as defined above and a pharmaceutically acceptable carrier.

Those active components of the present invention are preferably used in such a pharmaceutical composition, in doses mixed with an acceptable carrier or carrier material, that the disease can be treated or at least alleviated. Such a composition can (in addition to the active component and the carrier) include filling material, salts, buffer, stabilizers, solubilizers and other materials, which are known state of the art.

The term "pharmaceutically acceptable" defines a non-toxic material, which does not interfere with effectiveness of the biological activity of the active component. The choice of the carrier is dependent on the application.

The pharmaceutical composition can contain additional components which enhance the activity of the active component or which supplement the treatment. Such additional components and/or factors can be part of the pharmaceutical composition to achieve synergistic effects or to minimize adverse or unwanted effects.

Techniques for the formulation or preparation and application/medication of active components of the present invention are published in "Remington's Pharmaceutical Sciences", Mack Publishing Co., Easton, Pa., latest edition. An appropriate application is a parenteral application, for example intramuscular, subcutaneous, intramedular injections as well as intrathecal, direct intraventricular, intravenous, intranodal, intraperitoneal or intratumoral injections. The intravenous injection is the preferred treatment of a patient.

According to a preferred embodiment, the pharmaceutical composition is an infusion or an injection.

An injectable composition is a pharmaceutically acceptable fluid composition comprising at least one active ingredient, e.g., an expanded T-cell population (for example autologous or allogenic to the patient to be treated) expressing a TCR. The active ingredient is usually dissolved or suspended in a physiologically acceptable carrier, and the composition can additionally comprise minor amounts of one or more non-toxic auxiliary substances, such as emulsifying agents, preservatives, and pH buffering agents and the like. Such injectable compositions that are useful for use with the fusion proteins of this disclosure are conventional; appropriate formulations are well known to those of ordinary skill in the art.

In a further aspect, the present invention is directed to a method of treating a patient in need of adoptive cell therapy, said method comprising administering to said patient a pharmaceutical composition as defined above to said patient. The patient to be treated preferably belongs to the group of HLA-A2 positive patients.

Preferably, said patient suffers from a disease involving malignant cells expressing tyrosinase, preferably melanoma, glioma, glioblastoma, and/or rare tumors of ectodermal origin.

The present invention now will be illustrated by the enclosed Figures and the EXAMPLES. The following EXAMPLES further illustrate the invention but, of course, should not be construed as limiting its scope.

DESCRIPTION OF THE FIGURES

FIG. 1: Screening of clones obtained from limiting dilution cultures after DC priming. T cells were primed with dendritic cells expressing HLA-A2 and tyrosinase RNA. After two rounds of priming in vitro, cells were cloned by limiting dilution. 14 to 28 days later T cell clones showing adequate growth in individual culture wells were identified by light microscopy. Aliquots of growing clones were obtained and tested in a standard $^{51}$Cr release assay to measure their killing activity against two melanoma target cell lines. Mel-A375 cells express HLA-A2 but not tyrosinase. Mel-93.04A12 cells express HLA-A2 and tyrosinase, so they can form the ligands recognized by HLA-A2-restricted, tyrosinase peptide (YMDGTMSQV; SEQ ID NO: 9)-specific T cells. If Mel-A375 cells are recognized by T cell clones, this means the clones are alloreactive and recognize HLA-A2 independent of tyrosinase peptide (i.e., clone T41 and T42). If the T cell clones only recognize Mel-93.04A12, then they should have specificity for HLA-A2-tyrosinase peptide ligands (i.e. T58, T43). Percentage specific lysis mediated by various T cell clones, (listed on x-axis) is given for the two target melanoma cell lines. The arrow designates clone T58 which shows strong killing of Mel-93.04A12 but not of Mel-A375. This clone was selected for further characterization based on its strong growth capacity.

FIG. 2A: Cytotoxic activity directed against melanoma cell lines.

The killing capacity of clone T58 was compared with that of clone IVS-B, derived from a melanoma patient, using as target cells the T2 cell line pulsed with synthetic tyrosinase-peptide for the amino acid sequence YMDGTMSQV (SEQ ID NO: 9) in different molar concentrations, listed on the x-axis. The % relative lysis is given on the y-axis. The concentration of peptide that corresponds to 50% relative lysis is indicated by the crossing lines and shows that clone T58 can recognize substantially lower concentrations of peptide in comparison to clone IVS-B.

Figure 2A:
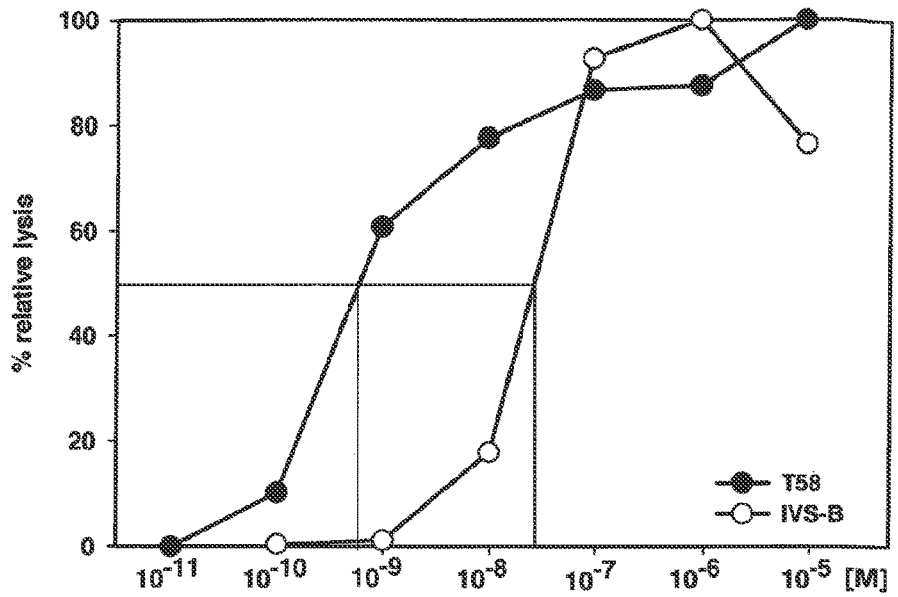
FIGS. 2A-2D: Comparison of clones T58 and IVS-B
Figure 2B:
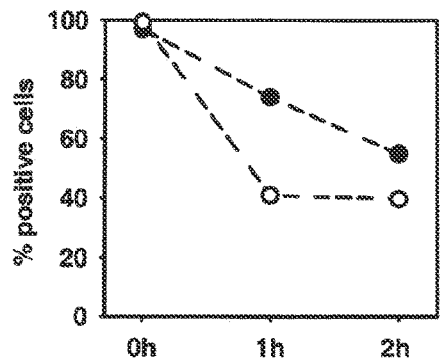

FIG. 2B: Measurement of multimer binding and off-rates.

The two clones were incubated with multimers to determine the percentage of positive cells at time 0 h. Both clones bound multimer on 100% of the cells. Multimer was washed out and the clones were incubated in medium containing HLA-A2-specific antibody. When multimers are released from the cell surface, they are captured by the antibody and can not rebind to the cells. The percent multimer-positive cells were reanalyzed at 1 h and 2 h.

Figure 2C:
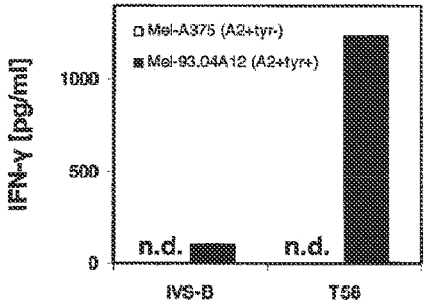

FIG. 2C: Interferon-gamma secretion after stimulation with melanoma cell lines.

Clone T58 and IVS-B were co-cultured with the two melanoma cell lines used for the initial screening (described in FIG. 1) and their secretion of IFN-γ into the culture medium was assessed by standard ELISA after 24 hours. n.d.=not detectable. Data are presented as pg/ml on the y-axis.

Figure 2D:
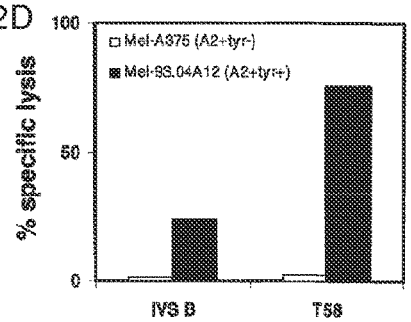

FIG. 2D: Cytotoxic activity against melanoma cell lines.

The clones were compared for killing activity using a standard $^{51}$Cr-release assay as described in FIG. 1. Data are given as percent specific lysis on the y-axis.

Figure 3A:
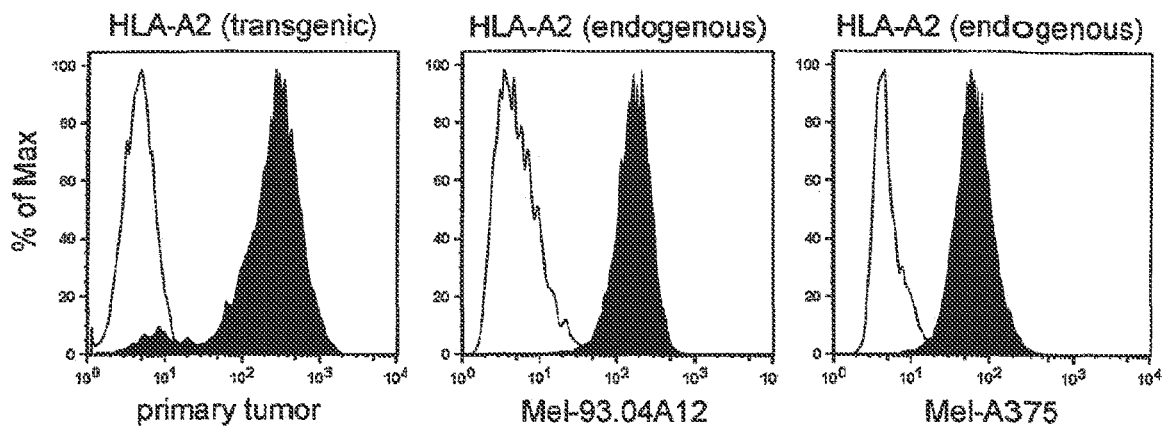
Figure 3B:
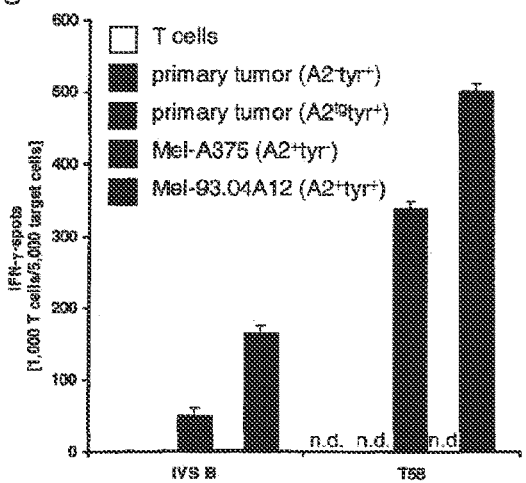
Figure 3C:
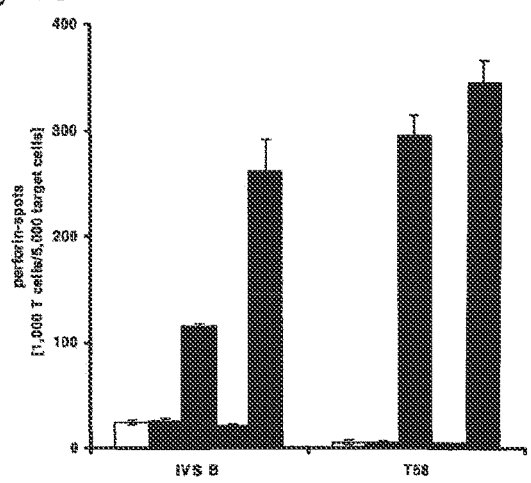

FIGS. 3A-3C: Recognition of primary melanoma tumor cells by clone T58 and IVS-B. (FIG. 3A) HLA-A2 surface expression on primary tumor cells (passage 12) of an HLA-A2$^-$ melanoma patient transfected with 50 μg HLA-A2 ivt-RNA and on established melanoma cell lines Mel-93.04A12 (HLA-A2$^+$tyrosinase$^+$) and Mel-A375 (HLA-A2$^+$ tyrosinase$^-$) was measured by flow cytometry after staining with HLA-A2-specific monoclonal antibody. Each histogram shows the stained sample (filled curves) and the corresponding control sample (empty curves): control curves represent untransfected primary tumor cells stained with HLA-A2-specific monoclonal antibody (left histogram) or melanoma cell lines stained with isotype control antibody. HLA-A2 protein expression on RNA-transfected primary tumor cells was detected 10 h after electroporation. (FIG. 3B) The capacity of the patient-derived T cell clone (IVS-B), and T cell clone T58 to secrete IFN-γ or (FIG. 3C) release perforin in co-culture with the melanoma cells shown above was measured in ELISPOT assays.

FIGS. 4A-4D: Transfer of antigen specificity by TCR retroviral gene transfer. (FIG. 4A) The human TCR-deficient T cell line Jurkat76[9] was transduced with the TCR of the T cell clone T58. TCR-expression was detected using tyrosinase-peptide-specific HLA-multimers. TCR expression was only detected in Jurkat76 cells tranduced with TCR-T58 (right histogram) and not in untransduced Jurkat76 cells (left histogram). (FIG. 4B) PBL of a healthy donor were retrovirally transduced with TCR-T58. After 10 days, untransduced and TCR-transduced PBL were analysed for tyrosinase TCR-expression using specific HLA-multimers. Multimer staining is shown on the x-axis and CD8 staining on the y-axis. The percentage of multimer$^+$CD8$^+$ T cells is displayed in the upper right quadrant. (FIG. 4C) Functionality of TCR-transduced PBL was measured using a standard IFN-γ release assay. T2 cells loaded with graded amounts of tyrosinase$_{369-377}$ peptide (YMDGTMSQV; SEQ ID NO: 9; $10^{-12}$ M-$10^{-5}$ M) were used as target cells at a fixed effector to target cell ratio of 1:1. Untransduced PBL served as a control and showed no tyrosinase-peptide specific IFN-γ release (data not shown). Data are shown as pg/ml cytokine after subtraction of secretion by untransduced PBL controls. (FIG. 4D) The capacity to secrete IFN-γ in co-culture with melanoma cell lines SK-Mel-28 (HLA-A2$^-$ tyrosinase$^+$), Mel-A375 (HLA-A2$^+$tyrosinase$^-$), Mel-624.38 (HLA-A2$^+$ tyrosinase$^+$) and Mel-93.04A12 (HLA-A2$^+$tyrosinase$^+$) was assessed using a standard IFN-γ release assay using an E:T=1:1; (n.d.=not detectable).

Figure 5A:
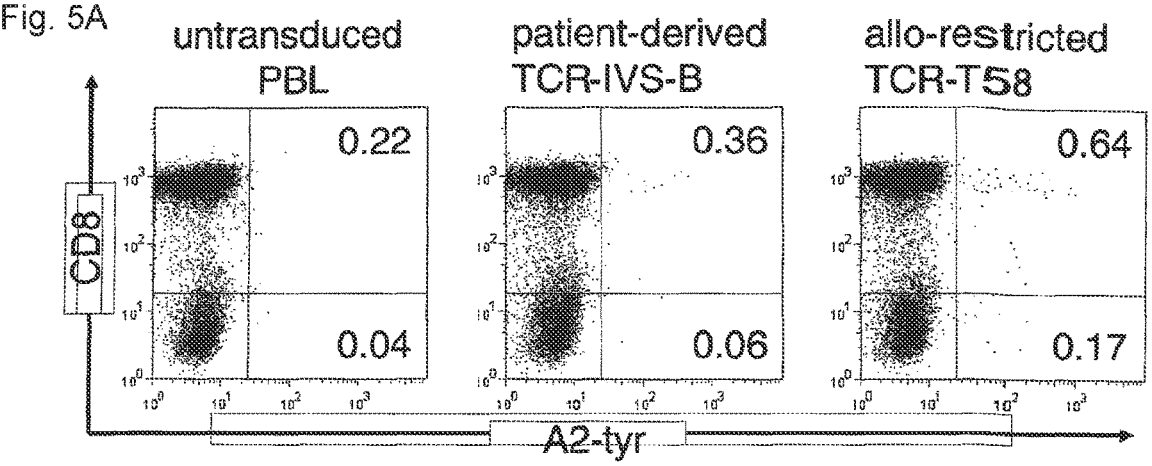
Figure 5B:
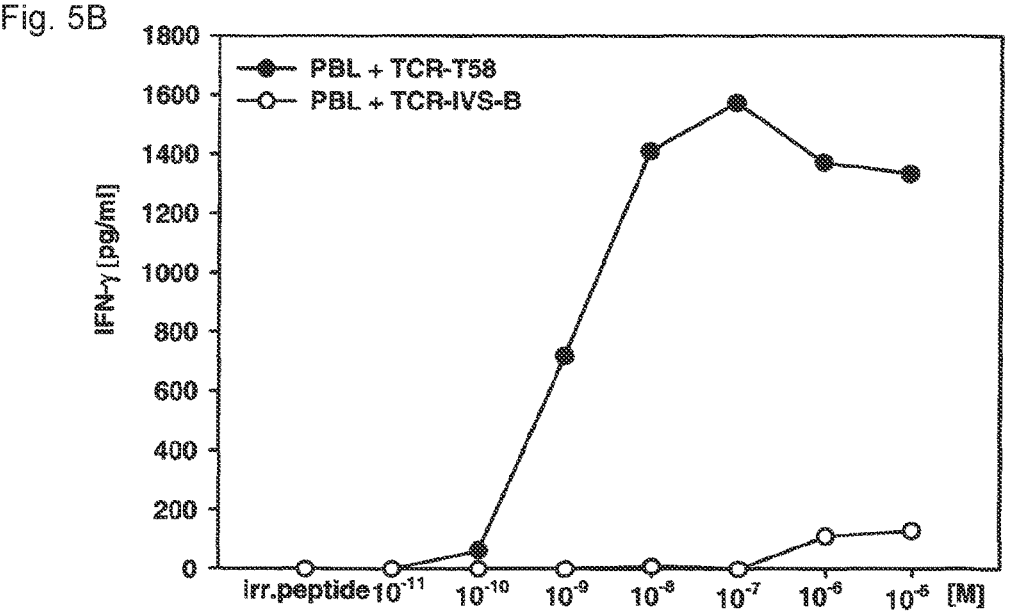

FIGS. 5A-5B: Transfer of specificity of T58 and IVS-B for HLA-A2 and tyrosinase-peptide YMDGTMSQV (SEQ ID NO: 9) by TCR retroviral gene transfer. (FIG. 5A) PBL of a healthy donor were retrovirally transduced with the patient-derived TCR-IVS—B or the TCR-T58. After 11 days, untransduced and TCR-transduced PBL were analysed for tyrosinase TCR-expression using specific HLA-multimers. Multimer staining is shown on the x-axis and CD8 staining on the y-axis. The percentage of multimer$^+$CD8$^+$ T cells is displayed in the upper right quadrant. (FIG. 5B) Functionality of TCR-transduced PBL was measured using a standard IFN-γ release assay. T2 cells loaded with graded amounts of tyrosinase$_{369-377}$ peptide ($10^{-11}$ M-$10^{-5}$ M) or with $10^{-5}$ M irrelevant influenza matrix protein$_{58-66}$ were used as target cells at a fixed effector to target cell ratio of 1:1.

Untransduced PBL served as a control and showed no tyrosinase-peptide specific IFN-γ release (data not shown). Data are shown as pg/ml cytokine after substration of secretion by untransduced PBL controls (mean=318 pg/ml; range=219-368 pg/ml) and adjustment for comparable numbers of multimer$^+$ cells.

Figure 6:
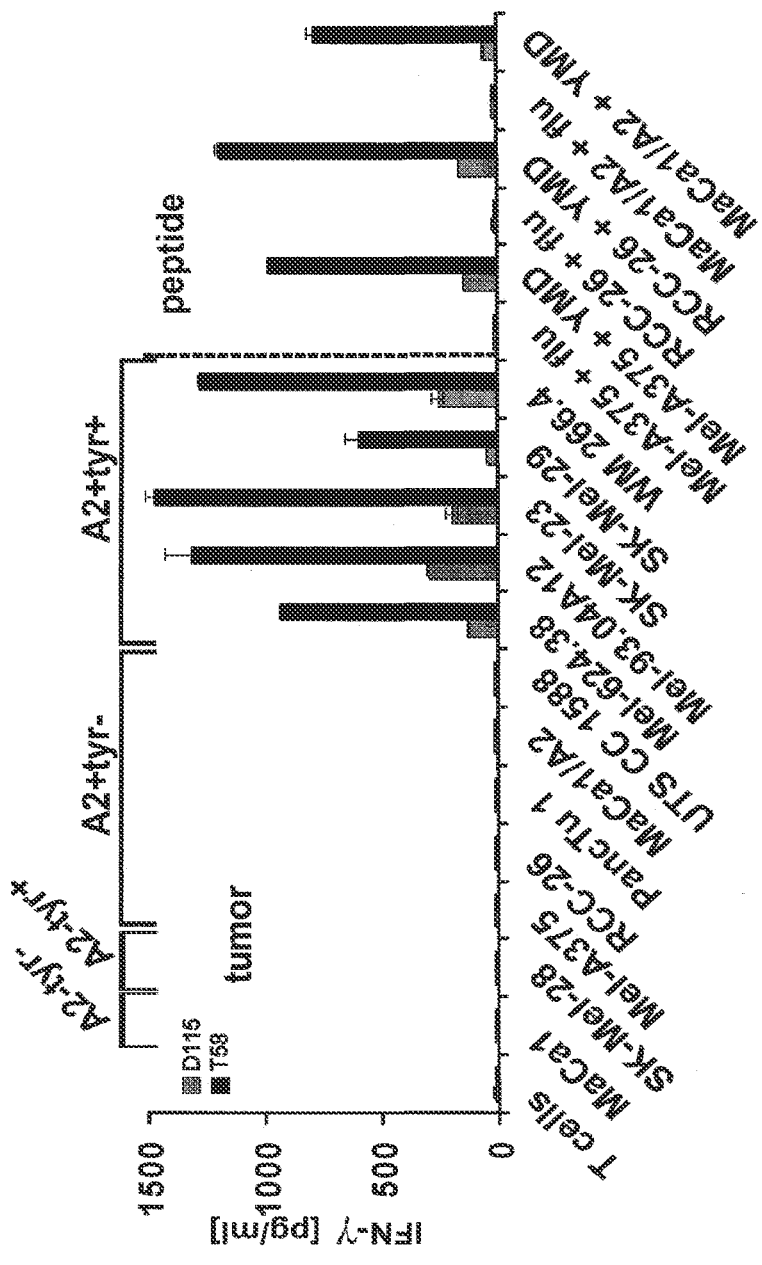

FIG. 6: Tyrosinase peptide-specific CTL recognition of tumor cell lines and primary melanoma tumor cells. Columns represent the amount of IFN-γ (pg/ml) secreted by self-restricted D115 CTL and allo-restricted T58 CTL in co-culture with a panel of tumor cell lines from left to right: MaCa1 (HLA-A2–tyrosinase–); SK-Mel-28 (HLA-A2–tyrosinase+); Mel-A375, RCC-26, PancTu 1, MaCa1/A2, and UTS CC 1588 (all HLA-A2+tyrosinase–); Mel-624.38, Mel-93.04A12, SK-Mel-23, SK-Mel-29 and WM-266-4 (all HLA-A2+tyrosinase+). T cells designates CTL without stimulating cells. The HLA-A2+tyrosinase– tumor cell lines Mel-A375, RCC-26 and MaCa1/A2 were exogenously loaded with either 10-5 M irrelevant flu peptide or 10-5 M tyrosinase peptide YMD and IFN-γ secretion was measured by ELISA and given as pg/ml.

Figure 7:
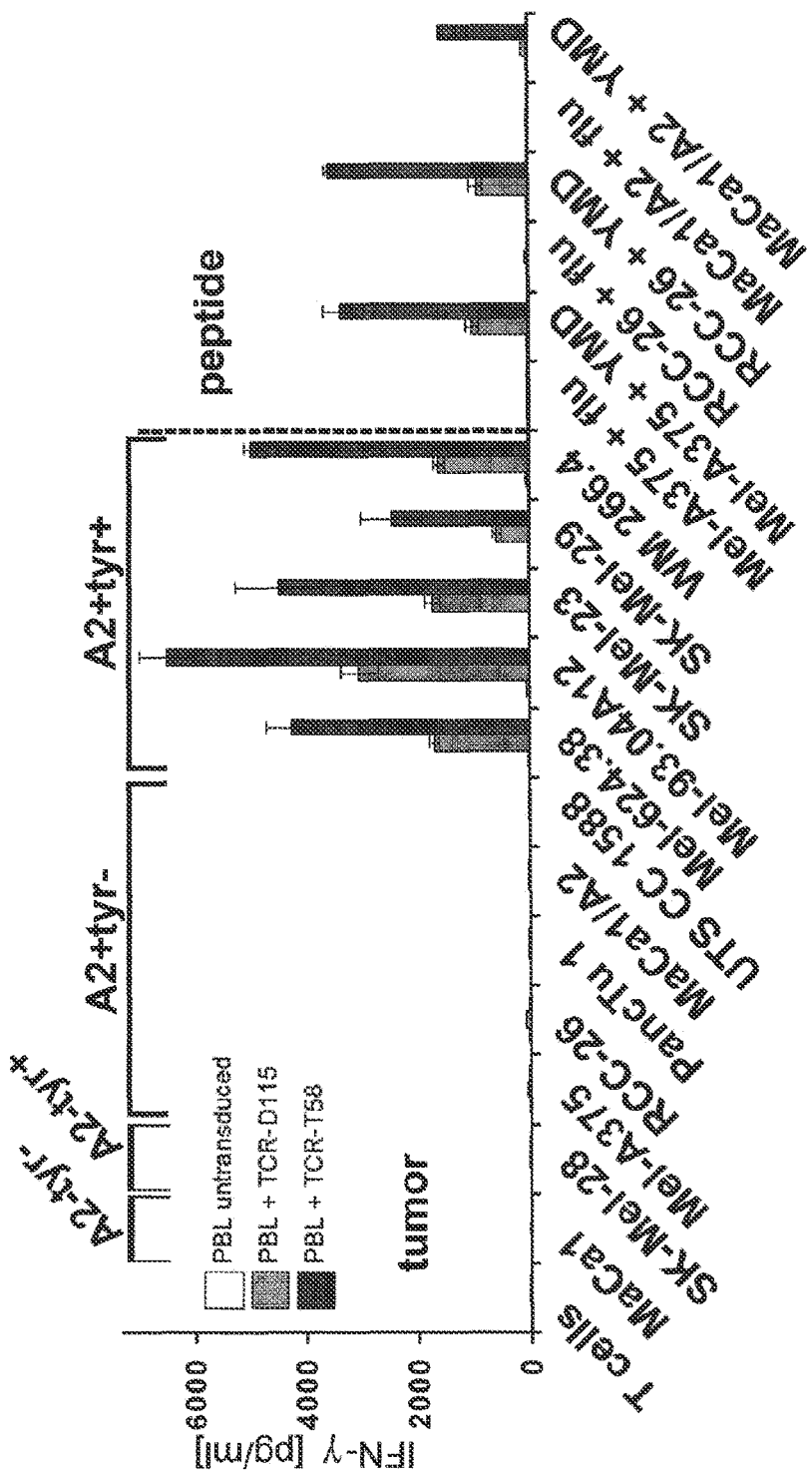

FIG. 7: Transfer of antigen specificity by retroviral transfer of TCR-D115 and TCR-T58. PBL of a healthy donor were transduced with TCR-D115 or TCR-T58. Specificity of recognition was assessed by IFN-γ release following co-culture with the tumor cell lines from left to right: MaCa1 (HLA-A2–tyrosinase–); SK-Mel-28 (HLA-A2–tyrosinase+); Mel-A375, RCC-26, PancTu 1, MaCa1/A2, and UTS CC 1588 (all HLA-A2+tyrosinase–); Mel-624.38, Mel-93.04A12, SK-Mel-23, SK-Mel-29 and WM-266-4 (all HLA-A2+tyrosinase+). T designates CTL without stimulating cells. The HLA-A2+tyrosinase– tumor cell lines Mel-A375, RCC-26 and MaCa1/A2 were exogenously loaded with either 10-5 M irrelevant flu peptide or 10-5 M tyrosinase peptide YMD and IFN-γ secretion was measured by ELISA and given as pg/ml.

FIGS. 8A-8F: Transfer of antigen specificity by retroviral transfer of TCR-D115 and TCR-T58. (FIG. 8A) PBL of a healthy donor were transduced with TCR-D115 or TCR-T58. Unsorted TCR-transduced PBL were analyzed on day 10 for transgenic TCR-expression using irrelevant B7-pp65 and A2-pp65 multimers and specific A2-tyr multimers. Untransduced PBL showed no multimer binding (0.1%, data not shown). Percentages of multimer+CD8+ T cells are displayed in the upper right quadrant. (FIGS. 8A and 8B) show the IFN-γ release of unsorted TCR-transduced PBL following stimulation with T2 cells loaded with graded amounts of tyrosinase peptide (10-12 M-10-5 M) at a ratio of 2:1. In FIG. 8B the relative IFN-γ release is displayed in percent and in FIG. 8C the specific IFN-γ release is presented as pg/ml. (FIG. 8D) Functionality of unsorted TCR-transduced PBL was measured by IFN-γ release using autologous HLA-A2+ PBMC loaded with tyrosinase peptide (10-11 M-10-6 M) as stimulating cells at ratio of 2:1. Untransduced PBL (▲) showed no peptide-specific IFN-γ release. (FIG. 8E) The HLA-A2+tyrosinase– tumor cell lines Mel-A375, RCC-26 and MaCa1/A2 were exogenously loaded with either 10-5 M irrelevant flu peptide (f) or 10-5 M tyrosinase peptide YMD (t) and IFN-γ secretion was measured by ELISA and given as pg/ml. (FIG. 8F) Specificity of recognition was assessed by IFN-γ release following co-culture with the tumor cell lines from left to right: MaCa1 (HLA-A2–tyrosinase–); SK-Mel-28 (HLA-A2–tyrosinase+); Mel-A375, RCC-26, PancTu 1, MaCa1/A2, and UTS CC 1588 (all HLA-A2+tyrosinase–); Mel-624.38, Mel-93.04A12, SK-Mel-23, SK-Mel-29 and WM-266-4 (all HLA-A2+tyrosinase+). T designates CTL without stimulating cells.

Figure 9A:
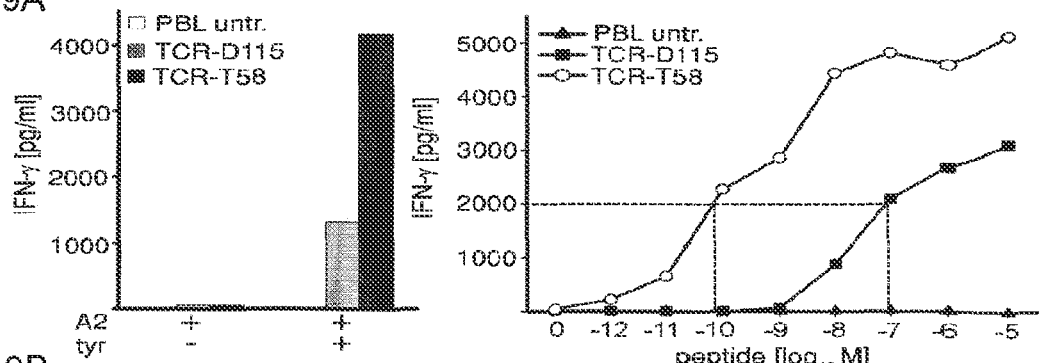
Figure 9B:
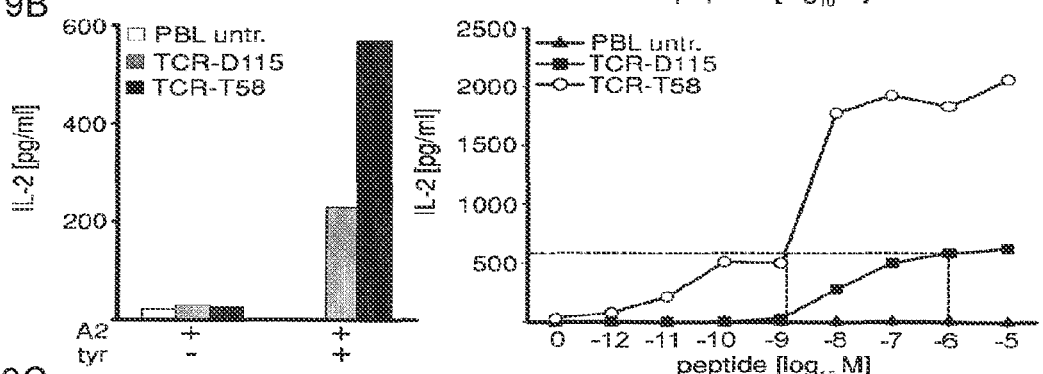
Figure 9C:
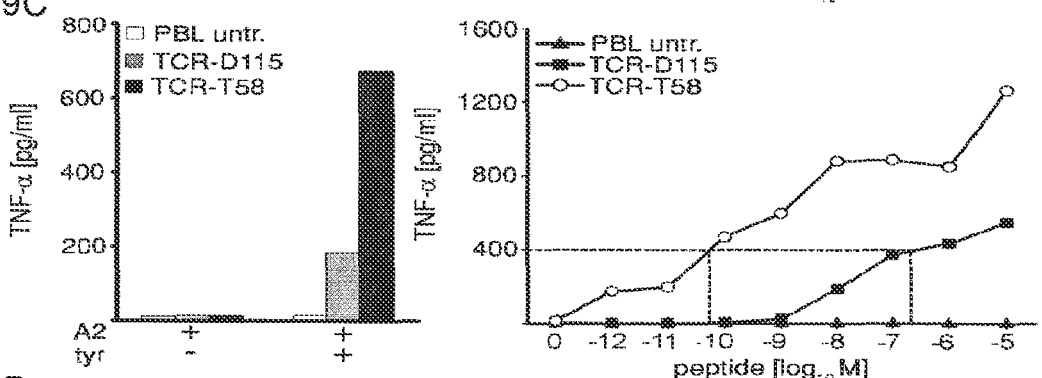
Figure 9D:
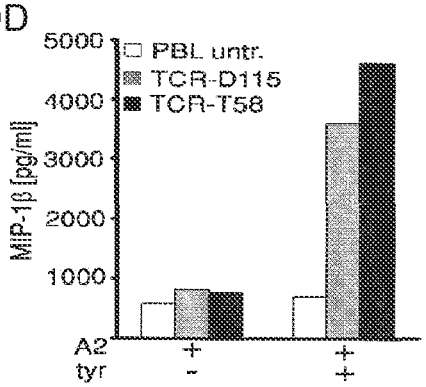

FIGS. 9A-9D: TCR transfer retains differences in cytokine profile. On the left hand side of FIGS. 9A-9D, the cytokine release of TCR-transduced PBL in co-culture with the melanoma lines Mel-A375 (HLA-A2+tyrosinase–) and Mel-624.38 (HLA-A2+tyrosinase+) is depicted, on the right hand side the corresponding cytokine release after stimulation with T2 cells loaded with graded amounts of tyrosinase peptide (10-12 M-10-5 M) is shown. Untransduced PBL (▲) showed no peptide-specific cytokine release. The following cytokines were measured: IFN-γ (FIG. 9A), IL-2 (FIG. 9B), TNF-α (FIG. 9C) and MIP-1β (FIG. 9D). The levels of cytokine secretion for all four cytokines were higher when PBL transduced with the allo-restricted TCR-T58 were used. Since untransduced PBL secreted very high levels of MIP- 1β in response to T2 cells the peptide titration for this cytokine could not be evaluated.

EXAMPLE 1

The inventors prepared stimulating dendritic cells (DC) from an HLA-A2-negative healthy donor that co-expressed allogeneic HLA-A*0201-molecules and tyrosinase protein using mature DC that were electroporated with in vitro transcribed (ivt)-RNA for tyrosinase and HLA-A2, as described[1,2]. These DC were used to prime purified, autologous CD8+ T cells using two rounds of stimulation with freshly prepared DC. After these two rounds of priming, CD8+ T cells with T cell receptors (TCR) recognizing HLA-A2-tyrosinase$_{369-377}$-peptide complexes were stained using a tyrosinase$_{369-377}$/HLA-A*0201-multimer[3]. CD8+ multimer+ cells were isolated by fluorescence activated cell sorting. Sorted cells were cloned in limiting dilution cultures and isolated clones showing HLA-A2/tyrosinase-peptide specificity were expanded using antigen-independent stimulation[4]. The T cell clone T58 was identified in an initial screen as having good functional activity (FIG. 1).

Because T58 was isolated from an HLA-A*0201-negative donor it represents an allo-restricted T cell clone that did not undergo negative selection in vivo. The activity of the T58 clone was compared with the IVS-B clone that was isolated from a patient with metastatic melanoma[5]. This clone recognizes exactly the same HLA-A2/tyrosinase peptide ligand as clone T58 but it is self-restricted since it was activated in vivo in the patient who was HLA-A*0201-positive. This patient-derived T cell clone represents an example of T cells that are available in the peripheral repertoire that have undergone negative selection against self-peptides/self-MHC-molecules in the thymus in vivo.

Side-by-side comparisons of clone T58 and clone IVS-B were made to demonstrate the superior properties of the allo-restricted T58 clone versus the self-restricted IVS-B clone. Functional T cell avidity for tyrosinase$_{369-377}$ peptide recognition was measured in a $^{51}$Cr-release assay using HLA-A2+ T2 cells pulsed with graded amounts of exogenous peptide as target cells. The peptide concentration needed for 50% relative lysis defined the value of half-maximum lysis[6]. The allo-restricted T cell clone T58 required substantially less peptide to be activated by peptide-pulsed T2 cells than clone IVS-B (6.0×10$^{-10}$ M vs. 3.0×10$^{-8}$ M) (FIG. 2A).

As an estimate of structural TCR-MHC/peptide binding affinity, loss of multimer binding was measured over time (i.e. HLA-multimer off-rate). A slower off-rate indicates that TCR-ligand interactions are more stable and of higher structural affinity[7]. After initial incubation with multimer and washing, T cells were incubated for 1 h and 2 h without multimers in the presence of HLA-A2-specific antibody to prevent cellular re-association of released multimers. The melanoma patient-derived T cell clone IVS-B showed an intermediate multimer binding: all cells were multimer+ at 0 h and about 40% retained multimers at 1 and 2 h (FIG. 2B). In contrast, clone T58 had a slower off-rate, showing 74% positive binding at 1 h versus 41% for clone IVS-B and even at 2 h still had somewhat more multimer+ cells (55% vs. 40%).

Both T cell clones were analyzed in an IFN-γ release assay for function and specificity (FIG. 2C). The clones were co-cultured with two melanoma cell lines that express HLA-A2 molecules but differ with respect to expression of tyrosinase protein: Mel-93.04A12 co-expresses both proteins (HLA-A2+tyrosinase+) but Mel-A375 fails to express tyrosinase protein (HLA-A2+tyrosinase−) and therefore can not generate the MHC-peptide ligand seen by the T cell clones. Allo-restricted T cell clone T58 was induced to secrete a high level of IFN-γ by the tyrosinase-expressing melanoma cell line, whereas only marginal cytokine secretion was seen with IVS-B cells (1,234 pg/ml vs. 106 pg/ml), demonstrating the vastly superior function of clone T58 in recognizing tumor cells expressing their HLA-A2-tyrosinase ligand. As expected, the clones showed no detectable IFN-γ secretion after stimulation with Mel-A375 cells, demonstrating the specificity for HLA-A2 and tyrosinase expression for tumor cell recognition.

The killing capacity of allo-restricted clone T58 was also compared with clone IVS-B using a $^{51}$Cr-release assay (FIG. 2D). Again, clone T58 showed superior function (76% vs. 24% specific lysis).

Both clones were also tested for their capacity to recognize primary melanoma cells. Since primary HLA-A2+ melanoma cells were not available, we introduced ivt-RNA for HLA-A2 into the tumor cells as for DC (FIG. 3A). Function was measured using ELISPOT assays detecting IFN-γ secretion and perforin release to bypass high spontaneous release of radioactive label by primary tumor cells. Recognition of primary tumor cells was shown to be HLA-A2-restricted since primary tumor cells lacking HLA-A2 RNA were not recognized. Again, a strong difference was observed with poor recognition by the patient self-restricted IVS-B cells versus good recognition by allo-restricted T58 cells as assessed with IFN-γ secretion (FIG. 3B) and by perform secretion (FIG. 3C).

Figure 4A:
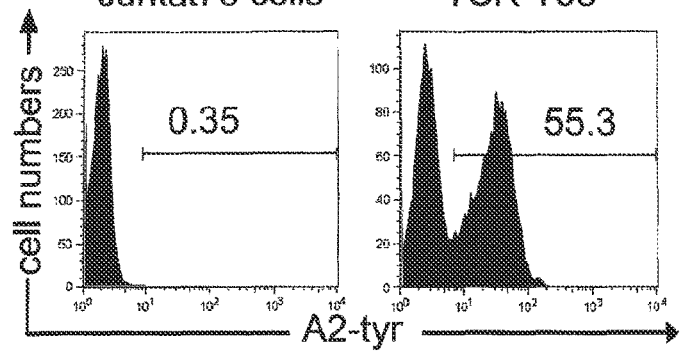
Figure 4B:
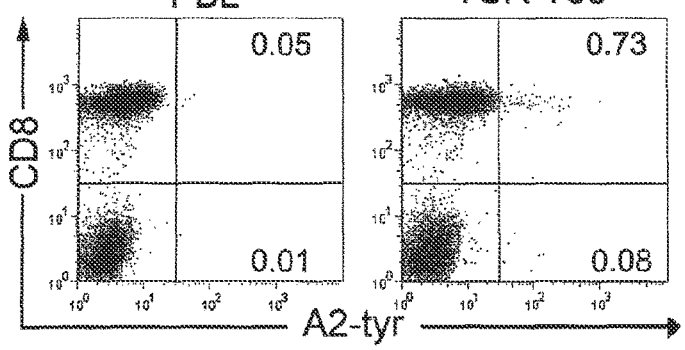
Figure 4C:
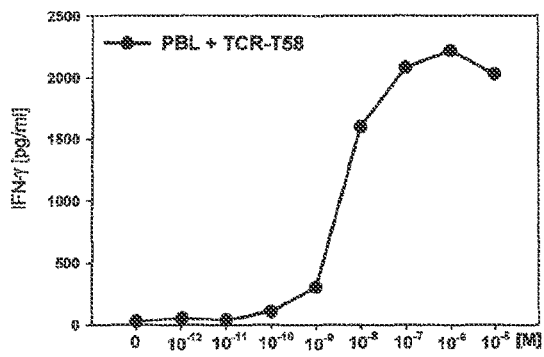
Figure 4D:
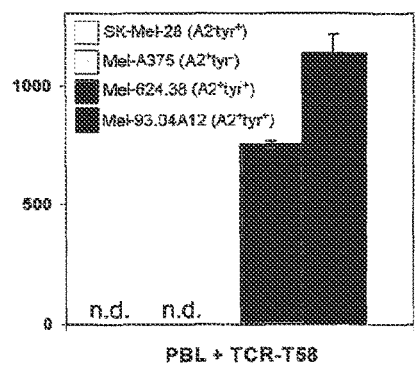

To demonstrate that the superior functional avidity of allo-restricted T58 cells resided directly in the TCR, separate recombinant retroviruses were created for TCR alpha and beta chains of clone T58 as described[8]. Human TCR-deficient Jurkat76 cells[9] were co-infected with the α-chain and β-chain retroviruses and transgenic TCR-expression was measured by multimer staining. TCR-T58 was expressed at a good level, demonstrating adequate quality of the separate retroviral supernatants (FIG. 4A). Next, activated peripheral blood lymphocytes (PBL) of a healthy HLA-A2− donor were transduced and analyzed with multimers for tyrosinase-specific TCR-expression (FIG. 4B). Despite this low frequency, PBL transduced with TCR-T58 released high amounts of IFN-γ following stimulation with T2 cells pulsed with graded amounts of tyrosinase-peptide (FIG. 4C). TCR-T58 transduced PBL could also respond specifically to stimulation by melanoma cell lines that expressed HLA-A2 and tyrosinase (FIG. 4D). They did not respond to tumor cells that did not express HLA-A2 or tyrosinase, again demonstrating the specificity of HLA-A2-tyrosinase ligands for T58 recognition.

Bi-cistronic retroviral vectors were also prepared encoding the α-chain and β-chains of the TCR of IVS-B cells and used to transduce activated PBL. In parallel, the same activated PBL were transduced with bi-cistronic retroviral vectors encoding the two chains of TCR-T58. PBL expressing the corresponding receptors were identified by co-staining for CD8 and multimer and showed low numbers of positive cells. (FIG. 5A) Despite their low frequency, PBL transduced with TCR-T58 released high amounts of IFN-γ following stimulation with T2 cells pulsed with graded amounts of tyrosinase-peptide. PBL expressing TCR-IVS-B secreted far less IFN-γ. Tyrosinase peptide-specific cytokine secretion was not detected with untransduced PBL control cells. Data are shown as pg/ml cytokine after substraction of secretion by untransduced PBL controls (mean=318; range=219-369 pg/ml) (FIG. 5B).

Table 1 shows the genetic information regarding the use of VJ and VDJ gene segments by the alpha and beta chains of TCR-T58, respectively. The CDR3 regions, according to IMGT, are presented as nucleotide sequences and amino acid sequences. Also shown are the codon optimized sequences for the full VJ and VDJ regions.

Materials and Methods

Cell Lines

The human melanoma cell lines, Mel-A375 (HLA-A2$^+$, tyrosinase$^-$; CRL-1619, American Type Culture Collection (ATCC), Bethesda, Md.), Mel-93.04A12 (HLA-A2$^+$, tyrosinase$^+$, gift of P. Schrier, Department of Immunohematology, Leiden University Hospital, The Netherlands), Mel-624.38[10] (HLA-A2$^+$, tyrosinase$^+$, gift of M. C. Panelli, National Institutes of Health, Bethesda, Md.), SK-Mel-28 (HLA-A2$^-$, tyrosinase$^+$; MTB-72, ATCC) as well as the lymphoid cell line T2 (CRL-1992, ATCC), and the human TCR-deficient Jurkat76[9] T cell line were cultured in RPMI 1640 medium supplemented with 12% fetal bovine serum (FBS), 2 mM L-glutamine and 1 mM sodium-pyruvate and non-essential amino acids.

The HLA-A*0201-restricted tyrosinase$_{369-377}$ peptide-specific melanoma patient-derived IVS-B T cell clone was cultured as described[5].

Production of Tyrosinase and HLA-A2 Ivt-RNA

The plasmid pCDM8-HLA-A2 with HLA-A*0201 cDNA and the pZeoSV2+/huTyr with tyrosinase cDNA were linearized and used as in vitro transcription templates to produce RNA with the aid of the mMESSAGE mMACHINE T7 kit (Ambion, Austin, Tex.) according to the manufacturer's instructions.

De Novo Priming of T Cells with RNA-pulsed DC

Blood samples from healthy donors were collected after informed consent and with approval of the Institutional Review Board of the University Hospital of the Ludwig-Maximilians-University, Munich, Germany. Peripheral blood lymphocytes (PBL) were isolated by Ficoll density gradient centrifugation. PBL were resuspended in 15 ml very low endotoxin (VLE) RPMI 1640 medium (Biochrom, Berlin, Germany) supplemented with 1.5% human serum (DC medium) at 7.5×10$^7$ cells per 75 cm$^2$ culture flask and incubated at 37° C. and 5% CO$_2$ for 1 h. Non-adherent cells were carefully removed by washing. Mature DC were prepared from adherent monocytes and transfected with ivt-RNA via electroporation as previously described[2]. DC of HLA-A2$^-$ donors were co-transfected with 24 µg tyrosinase ivt-RNA and 48 µg HLA-A2 ivt-RNA. On the same day, autologous CD8$^+$ T lymphocytes were enriched from PBL via negative selection using a commercial kit according to the manufacturer's instructions (CD8$^+$ T cell Isolation Kit II (human), Miltenyi, Bergisch Gladbach, Germany). Co-cultures were initiated 10 h after DC electroporation in 24-well plates (TPP, Trasadingen, Switzerland) by adding 1×10$^5$ RNA-pulsed DC to 1×10$^6$ CD8$^+$ T cells in RPMI 1640, supplemented with 10% heat-inactivated human serum, 4 mM L-glutamine, 12.5 mM HEPES, 50 µM 3-mercaptoethanol and 100 U/ml penicillin/streptomycin (T cell medium). IL-7 (5 ng/ml) (Promokine, Heidelberg, Germany) was added on day 0 and 50 U/ml IL-2 (Chiron Behring, Marburg, Germany) was added after 2 days and then on every 3$^{rd}$ subsequent day. Addition of IL-2 was delayed to decrease proliferation of non-specific CD8$^+$ T cells[4]. The 2$^{nd}$ stimulation of primed T cells was made after seven days using freshly prepared RNA-pulsed DC.

HLA-multimer Staining and Sorting

Seven days after the 2$^{nd}$ stimulation of CD8-enriched T cells with RNA-pulsed DC, HLA-A2-restricted tyrosinase-specific T cells were detected by staining with a PE-labeled HLA-A*0201/htyr$_{369-377}$ peptide/human β$_2$m multimer[11], anti-CD8-APC antibody (clone RPA-T8, BD Pharmingen, Franklin Lakes, N.J.) and propidium iodide (PI: 2 µg/ml). For sorting, up to 5×10$^6$ cells were incubated with 12 µg multimer in 100 µl PBS+0.5% human serum. CD8-APC antibody was then added at 1/50 for an additional 25 min. After staining cells were washed twice and diluted in PBS+0.5% human serum with PI for sorting. 20-50×10$^6$ total cells per priming culture were stained for sorting. PI-negative cells were gated and CD8$^+$multimer$^+$ T cells were sorted on a FACSAria cell sorter (BD Biosciences) with a 70 µm nozzle, at a rate of 15,000 events/s.

For HLA-multimer off-rate assays, cells were washed after multimer binding and resuspended in FACS buffer containing saturating amounts of BB7.2 monoclonal antibody (ATCC) to capture detached multimers and prevent rebinding to T cells. After 1 or 2 h, samples were fixed in FACS buffer with 1% paraformaldehyde and analysed by flow cytometry[7].

Culture of Peptide-specific T Clones

Multimer-sorted T cells were cloned by limiting dilution. Clones were plated in 96-well round-bottom plates (TPP) in 200 µl/well T cell medium. 50 IU/ml IL-2 was supplemented every 3 days with 5 ng/ml IL-7 and 10 ng/ml IL-15 (PeproTech Inc., Rocky Hill, N.J.) every 7 days. T cell clones were stimulated non-specifically with anti-CD3 antibody (0.1 µg/ml; OKT-3) and provided with 1×10$^5$ feeder cells per 96-well, consisting of irradiated (50 Gy) PBL derived from a pool of five unrelated donors and 1×10$^4$ irradiated (150 Gy) EBV-transformed allogeneic B-LCL every two weeks. Proliferating T cells were transferred into 24-well plates (TPP) and cultured in 1.5 ml T cell medium plus cytokines. 1×10$^6$ allogeneic irradiated PBL and 1×10$^5$ irradiated EBV-transformed allogeneic B-LCL were added per well as feeder cells in 24-well plates. Clonality was determined by TCR-beta-chain receptor analysis, as described[12].

Peptide Loading of T2 Cells

For exogenous peptide pulsing, 1×10$^6$ T2 cells were incubated at 37° C. and 5% CO$_2$ for 2 h with 10 µg/ml human β$_2$-microglobulin (Calbiochem, San Diego, Calif.) and titrating amounts, ranging from 10$^{-5}$ M to 10$^{-12}$ M, of the tyrosinase peptide YMD (tyrosinase$_{369-377}$ YMDGTMSQV, SEQ ID NO: 9, Metabion, Martinsried, Germany). T2 cells pulsed with 10$^{-5}$ M influenza peptide GIL (influenza matrix protein$_{58-66}$ GILGFVTL, SEQ ID NO: 10, Metabion) served as negative control. After washing, peptide-loaded T2 cells were used as target cells in cytotoxicity or IFN-γ-release assays.

IFN-γ Release Assay

For investigation of specificity, T cell clones (2×10$^3$ cells in 100 µl) were incubated with the respective melanoma cell lines or peptide-pulsed T2 cells (1×10$^4$ cells in 100 µl). Culture supernatants were harvested after 24 h co-culture and assessed by a standard ELISA using the OptEIA™ Human IFN-γ Set (BD Biosciences Pharmingen).

Cytotoxicity Assay

Cytotoxic activity of T cell clones was analysed in a standard 4 h 51-chromium release assay. Melanoma cells or peptide-loaded T2 cells were used as target cells. Briefly, 1×10$^6$ target cells were labeled with 100 µCi Na$_2^{51}$CrO$_4$ (ICN Biochemicals, Irvine, Calif.) for 1-1.5 h. $^{51}$Cr-labeled target cells were cultured with T cells in 100 µl/well RPMI 1640 with 12% FCS in V-bottom 96-well tissue culture plates (Greiner, Solingen, Germany). For determination of functional avidity 1×10$^4$ T cells were added to 1×10$^3$ peptide-pulsed T2 cells loaded with titrated amounts of peptide, giving a constant E:T of 10:1.

After 4 h co-culture at 37° C., 50 µl of supernatant were collected and radioactivity was measured in a gamma counter. The percentage of specific lysis was calculated as: 100×(experimental release−spontaneous release)/(maximum release−spontaneous release). Spontaneous release was assessed by incubating target cells in the absence of effector cells and was generally less than 15%. For the calculation of percent relative lysis, the maximum percent specific lysis was set to the reference value of 100% and corresponding values were calculated corresponding to this reference. To determine half-maximum lysis, percent relative lysis was plotted against peptide concentration. The peptide concentration at which the curve crossed 50% relative lysis was taken as the value of half-maximum lysis[6].

ELISPOT

Antibody pre-coated PVDF plates (Mabtech AB, Nacka, Sweden) were incubated at 37° C. in CTL Test™ medium (Cellular Technology Ltd., Cleveland, Ohio) for 2 h to block unspecific binding. For the IFN-γ ELISPOT, plates were pre-coated with the IFN-γ-specific capture antibody clone 1-D1K; for perforin ELISPOT plates were pre-coated with the perforin-specific capture antibody (clone Pf-80/164; Mabtech AB). Primed T cells were washed with CTL Wash™ Supplement culture medium (Cellular Technology Ltd) and $1 \times 10^3$ responder T cells were stimulated with $5 \times 10^3$ melanoma cells in 150 µl CTL Test™ medium and 24 h later assessed in IFN-γ ELISPOT or 48 h later in perforin ELISPOT. After washing with PBS/0.01% Tween and PBS alone, plates were incubated either with a direct streptavidin-alkaline phosphatase (ALP)-conjugated detection antibody (clone 7-B6-1; Mabtech AB) for IFN-γ ELISPOT or with biotinylated detection antibody (clone Pf-344; Mabtech AB) for perforin ELISPOT for 2 h at room temperature following a 1 h incubation with streptavidin-alkaline phosphatase (ALP). The plates were washed again and a ready-to-use BCIP/NBT-plus substrate solution (Mabtech AB) was added. Spots were counted using the AID reader system ELR03 with the software version 4.0 (AID Autoimmun Diagnostika GmbH, Strassberg, Germany).

Construction of Retroviral Vectors, Production of Virus Supernatants and Transduction of Jurkat76 T Cells and PBL For TCR identification of tumor-specific T cell clones, part of the TCRα- and TCRβ-chain sequences including the complementary determining region (CDR3) was amplified by PCR using a panel of TCRVα and TCRVβ primers combined with the respective constant region primer as described[13]. The TCRα and TCRβ chain genes of T cell clones T58 and IVS-B were amplified by PCR with gene specific primers and cloned into the retroviral vector MP71PRE[8] via NotI and EcoRI restriction sites. Both chains of human TCR-T58 (Vα7, Vβ23) and TCR-IVS-B (Vα3, Vβ14) were constructed as single-TCR gene vectors or double-TCR gene vectors (pMP71-T58α and pMP71-T58β, pMP71-IVS-Bα and pMP71-IVS-Bβ; pMP71-T58β-P2A-T58α and pMP71-IVS-Bβ-P2A-IVS-Bα). Retroviral vector plasmids were co-transfected into 293T cells with expression plasmids encoding Moloney MLV gag/pol and MLV-10A1 env gene to produce amphotropic MLV-pseudotyped retroviruses as described[14]. The human TCR-deficient T cell line Jurkat76 and PBL were transduced as reported[14]. Jurkat76 cells (5 days after transduction) and PBL (10 days after transduction) were stained using PE-labeled HLA-A*0201/htyr$_{369-377}$ peptide/human β$_2$m multimer and anti-CD8-FITC antibody. On day 13 an IFN-γ release assay was performed using T2 cells loaded with graded amounts of tyrosinase$_{369-377}$ peptide ($10^{-12}$ M-$10^{-5}$ M) or T2 cells pulsed with $10^{-5}$ M influenza matrix protein$_{58-66}$ peptide and the tumor cell lines SK-Mel-28, Mel-A375, Mel-624.38 and Mel-93.04A12 as stimulating cells at an E:T ratio=1:1. Control values for peptide-stimulated untransduced PBL were subtracted from values of transduced cells at each peptide concentration and then adjusted to comparable numbers of total TCR-transgenic cells.

T58-TCR Analysis

For the T-cell receptor analysis of the tyrosinase-specific clone T58, part of the TCR alpha-chain and beta-chain containing the CDR3 region was amplified by RT-PCR using a panel of TCR Vα and TCR Vβ primers combined with a respective TCR constant region primer. Products were sequenced and assigned according to IMGT (Table 1; IMGT, THE INTERNATIONAL IMMUNOGENETICS INFORMATION SYSTEM®).

Modifications of the TCR-sequence

Codon optimization of the VJ/VDJ-regions of both T58-TCR chains was done to facilitate TCR mRNA translation (Table 1). Antibody-tags, for example myc-tags[15] (Patent Application number: 06014606.5-1212) or other modifications, for example a CD20 epitope, can be introduced in any position, i.e. the N-terminus of the TCRα-chain, that is recognized by the depleting antibody and does not interfere with TCR-functionality.

TABLE 1

TCR-CDR3 sequences and codon optimized VJ/VDJ regions of clone T58

| Alpha-chain | |
|---|---|
| VJ region* | |
| CDR3 region* | TRAV1-2 AJ28 |
| Nucleotide sequence | TGTGCTGTGACATACTCTGGGGCTGGGAGTTACCAACTC (SEQ ID NO: 3) |
| Amino acid sequence | CAVTYSGAGSYQL (SEQ ID NO: 5) |
| Codon optimized VJ | ATGTGGGGCGTGTTTCTGCTGTACGTGTCCATGAAGA<br>TGGGCGGCACCACCGGCCAGAACATCGACCAGCCCA<br>CCGAGATGACAGCCACCGAGGGCGCCATCGTGCAGA<br>TCAACTGCACCTACCAGACCAGCGGCTTCAACGGCCT<br>GTTCTGGTATCAGCAGCACGCCGGCGAGGCCCCTACC<br>TTCCTGAGCTACAACGTGCTGGACGCCTGGAAGAG<br>AAGGGCCGGTTCAGCAGCTTCCTGAGCCGGTCCAAG<br>GGCTACAGCTACCTGCTGCTGAAAGAACTGCAGATG<br>AAGGACAGCGCCAGCTACCTGTGCGCCGTGACCTAC |

TABLE 1-continued

TCR-CDR3 sequences and codon optimized VJ/VDJ regions of clone T58

| | |
|---|---|
| | AGCGGAGCCGGCAGCTACCAGCTGACCTTCGGCAAG<br>GGCACCAAGCTGTCCGTG (SEQ ID NO: 7) |
| Beta-chain | |
| VDJ region* | |
| CDR3 region* | TRBV13 BD1 BJ1-4 |
| Nucleotide sequence | TGTGCCAGCAGTCAGAAACAGGGCTGGGAAAAAC<br>TG<br>(SEQ ID NO: 4) |
| Amino acid sequence | CASSQKQGWEKL (SEQ ID NO: 6) |
| Codon optimized VDJ | ATGCTGTCCCCCGATCTGCCCGACAGCGCCTGGAA<br>CACCAGACTGCTGTGCCACGTGATGCTGTGTCTGC<br>TGGGAGCCGGATCTGTGGCCGCTGGCGTGATCCA<br>GAGCCCCAGACACCTGATCAAAGAGAAGCGGGAG<br>ACAGCCACCCTGAAGTGCTACCCCATCCCCCGGC<br>ACGACACCGTGTACTGGTATCAGCAGGGACCAGG<br>ACAGGACCCCCAGTTCCTGATCAGCTTCTACGAGA<br>AGATGCAGAGCGACAAGGGCAGCATCCCCGACAG<br>ATTCAGCGCCCAGCAGTTCAGCGACTACCACAGC<br>GAGCTGAACATGAGCAGCCTGGAACTGGGCGACT<br>CTGCCCTGTACTTCTGCGCCAGCAGCCAGAAGCA<br>GGGCTGGGAGAAGCTGTTCTTCGGCAGCGGCACC<br>CAGCTGTCCGTGCTG (SEQ ID NO: 8) |

TCR alpha-chain (VJ region), TCR beta-chain (VDJ region) and CDR3 lengths are designated according to IMGT (IMGT, THE INTERNATIONAL IMMUNOGENETICS INFORMATION SYSTEM®)

EXAMPLE 2

In EXAMPLE 1, data are provided that compared two T cell clones that specifically recognize a peptide derived from tyrosinase (i.e., YMDGTMSQV (SEQ ID NO: 9) hereafter referred to as YMD) presented by HLA-A*0201 molecules. The T cell clone T58 was an allo-restricted, peptide-specific T cell clone derived from an HLA-A2-negative donor. The T cell clone IVS-B was derived from an HLA-A*0201-positive patient who suffered from metastatic melanoma. This melanoma expressed tyrosinase.

In this EXAMPLE, comparisons have been extended to include an example of a T cell clone, D115, which is also derived from an HLA-A*0201-positive individual and recognizes the same YMD peptide. However, in contrast to clone IVS-B, clone D115 was generated in vitro using responding T cells derived from the blood of a healthy individual. Therefore, there have been no potential negative impacts on this T cell clone from a tumor environment (i.e., melanoma) in vivo.

FIG. 6 shows a comparison of the pattern of the target cell recognition of the new clone D115 and clone T58 which is the subject of this patent. As can be clearly seen, both D115 and T58 show the same pattern of recognition, detected by secretion of interferon-gamma (y-axis), after co-cultivation with various tumor cell lines (x-axis and figure legend). Neither clone recognizes tumor cells that are HLA-A2-negative but express tyrosinase, nor do they recognize tumor cells that are HLA-A2-positive and tyrosinase negative. On the other hand, both T cell clones recognize several tumor cell lines that are both HLA-A2-positive and tyrosinase-positive. The role of the YMD peptide in this recognition is shown by the finding that HLA-A2-positive tumor cells that do not express tyrosinase from which the YMD peptide could be processed internally and transported to the cell surface by HLA-A2 molecules for presentation, can be loaded with synthetic YMD peptide, leading to their recognition by D115 and T58. Thereby, both clones show the same specificity for the YMD peptide presented by HLA-A2 molecules. However, the efficiency of recognition displayed by clone T58 is far superior to clone D115, as seen by the levels of interferon-gamma secretion. This, for example, leads to negligible recognition of the melanoma cell line SK-Mel-29 by D115 but clear recognition by T58.

The TCR of clone D115 and T58 were expressed as recombinant proteins in activated recipient lymphocytes (FIG. 7). When these TCR-transduced lymphocytes were retested with the same panel of target cells, they showed the same specificity pattern as the original T cell clones, demonstrating that the TCR recognition was responsible for the results seen in FIG. 6. Again, in FIG. 7 it is demonstrated that the TCR of clone T58 shows superior recognition of the melanoma tumor cell lines that express HLA-A2 and tyrosinase and the YMD peptide-pulsed HLA-A2-positive tumor cells.

FIG. 8A shows that the TCR-transduced lymphocytes show comparable levels of expression of the respective recombinant TCRs, with each transduced population having around 11% of T cells that bind a MHC multimer comprised of HLA-A2 molecules presenting the YMD peptide. Such binding is not observed with control multimers that present other peptides derived from the pp65 protein of human cytomegalovirus.

When the two populations of TCR-transduced PBL are stimulated with HLA-A2-positive antigen-presenting cells (i.e., T2 cells) that are pulsed with different concentrations of YMD peptide (shown on the x-axis), it can be seen that the cells expressing TCR-T58 release 50% of their maximal levels of interferon-gamma (y-axis) at 100-fold lower peptide concentrations. This peptide-sensitivity assay shows that the TCR-T58 has a much higher functional avidity when compared to TCR-D115 (FIG. 8B).

This difference is further exemplified by the strong difference in the maximum levels of interferon-gamma produced by the TCR-T58- versus TCR-D115-transduced lymphocytes. In the case of TCR-T58 cells, the maximum reaches 5000 pg/ml whereas this results in only around 2000 pg/ml for TCR-D115 in 24 hours. Furthermore, the amount of peptide that must be presented by T2 cells to cause release of 2000 pg/ml interferon-gamma is 15,000-fold lower for triggering of this level of response from TCR-T58-transduced lymphocytes compared with TCR-D115-transduced lymphocytes (FIG. 8C).

FIG. 8D shows another peptide-sensitivity assay, this time using peripheral blood mononuclear cells that have been pulsed with titrating amounts of YMD peptide (x-axis). Once again, the amounts of interferon-gamma released by lymphocytes expressing TCR-T58 are much greater compared with TCR-D115. The arrows show that the first detection of cytokine secretion occurs with 1000-fold less peptide for TCR-T58 compared with TCR-D115.

FIGS. 8E and 8F demonstrate the specificity of the transduced lymphocyte populations for peptide-pulsed tumor cells (FIG. 8E) or tumor cell lines expressing HLA-A2 and tyrosinase (FIG. 8F). In all cases, recognition is superior by lymphocytes expressing TCR-T58 compared to TCR-D115.

The superior secretion of cytokine is not limited to interferon-gamma. The levels of secretion of interleukin-2, TNF-alpha and MIP-1beta are also superior for TCR-T58. This is seen after stimulation of the TCR-transduced lymphocytes by tumor cells or by peptide-pulsed T2 cells (FIGS. 9A-9D).

Material and Methods

Cell Lines

The human melanoma cell lines, Mel-A375 (HLA-A2$^+$, tyrosinase$^-$; CRL-1619, American Type Culture Collection (ATCC)), Mel-93.04A12 (HLA-A2$^+$, tyrosinase$^+$; gift of P. Schrier, Department of Immunohematology, Leiden University Hospital, The Netherlands), Mel-624.38[1] and SK-Mel-23 (HLA-A2$^+$, tyrosinase; gift of M. C. Panelli, National Institutes of Health, Bethesda, Md.), SK-Mel-28 (HLA-A2$^-$, tyrosinase$^+$; MTB-72, ATCC), SK-Mel-29 (HLA-A2$_+$, tyrosinase$^+$, gift of P. Rieber, Institute of Immunology, Technical University Dresden, Germany), WM-266-4 (HLA-A2$^+$, tyrosinase$^+$; CRL-1676, ATCC) and primary cultures of a human melanoma (passage 6-12) and MaCa1 (HLA-A2$^-$, tyrosinase$^-$, gift of R. Wank, M.D. Munich, Germany), stable HLA-A*0201 transfectant of MaCa1 (MaCa1/A2) (HLA-A2$^+$, tyrosinase$^-$, gift of E. Noessner, Institute of Molecular Immunology, Helmholtz Zentrum München, Germany), RCC-26[2] (HLA-A2$^+$, tyrosinase$^-$), PancTu1 (HLA-A2$^+$, tyrosinase$^-$, gift of P. Nelson, Department for Biological Chemistry University Hospital LMU Munich, Germany), UTS CC 1588 (HLA-A2$^+$, tyrosinase$^-$, gift of M. Schmitz, Institute of Immunology, Technical University Dresden, Germany) as well as the lymphoid cell line T2 (CRL-1992, ATCC) were cultured in RPMI 1640 medium supplemented with 12% fetal bovine serum (FBS), 2 mM L-glutamine and 1 mM sodium-pyruvate and non-essential amino acids.

Peptide Loading of T2 Cells, PBMC and Tumor Cells

For exogenous peptide pulsing, $1 \times 10^6$ T2 cells were incubated at 37° C. and 5% $CO_2$ for 2 h with 10 µg/ml human β2-microglobulin (Calbiochem) and titrating amounts, ranging from $10^{-5}$ M to $10^{-11}$ M, of the tyrosinase peptide YMD (tyrosinase$_{369-377}$ YMDGTMSQV, SEQ ID NO: 9, Metabion). T2 cells pulsed with $10^{-5}$ M influenza peptide GIL (flu: influenza matrix protein$_{58-66}$ GILG-FVFTL, SEQ ID NO: 10, Metabion) served as the negative control. PBMC were loaded with tyrosinase peptide as for T2 cells with titrating amounts ranging from $10^{-6}$ to $10^{-11}$ M. Tumor cells were loaded with either $10^{-5}$ M flu peptide or $10^{-5}$ M tyrosinase peptide YMD as described for T2 cells. After washing, peptide-loaded T2 cells, PBMC or tumor cells were used as stimulating cells in IFN-γ release assays.

Cytokine Assays

For investigation of specificity, CTL ($2 \times 10^3$ cells in 100 µl) were incubated with various tumor cell lines ($1 \times 10^4$ cells in 100 µl), with or without peptide pulsing, as described above. Culture supernatants were harvested after 24 h co-culture and assessed by a standard ELISA using the OptEIA™ Human IFN-γ Set (BD Biosciences). Data represent mean values with corresponding mean deviations calculated from duplicate determinations. For the calculation of % relative IFN-γ release, the maximum IFN-γ release was set to the reference value of 100% and corresponding values were calculated corresponding to this reference.

To investigate multiple cytokines simultaneously (IFN-γ, IL-2, TNF-α and MIP-1β) cytokine secretion in supernatants of co-culture of CTL with tumor cells and with or without tyrosinase peptide pulsed T2 cells ($10^{-5}$ M) was measured using the multiplex protein array system technology (Bio-Rad Laboratories, Hercules, Calif.).

Retroviral TCR Gene Transfer

For TCR identification of tumor-specific CTL, regions of the TCRα- and TCRβ-chains encoding CDR3 were amplified by PCR using a panel of TCRVα and TCRVβ primers in combination with respective constant region primers as described.[3] The full TCRα- and TCRβ-chain genes of CTL clones T58 and D115 were amplified by PCR using cDNA as template. Primer sequences will be provided on request. The constant regions of both TCR chains were exchanged by the murine counterparts to increase the stability of the TCR.[4] The TCR chains were linked by a 2A peptide linker (TCRβ-P2A-TCRα)[5], codon-optimized (Geneart)[6] and cloned into the retroviral vector MP71PRE via NotI and EcoRI restriction sites.[5] Retroviral vector plasmids were co-transfected into 293T cells with expression plasmids encoding Moloney MLV gag/pol and MLV-10A1 env gene, respectively, to produce amphotropic MLV-pseudotyped retroviruses as described.[5] Ten days after the second transduction, PBL were stained using PE-labeled A2-tyr multimer and FITC-labeled CD8-specific antibody. Multimers presenting peptides derived from cytomegalovirus pp65 were used as controls: PE-labeled HLA-B7 pp65417-427 (B7-pp65) multimers served as the HLA control and HLA-A2 pp65495-503 multimers as a peptide-specificity control. On day 15 an IFN-γ release assay was performed using T2 cells or autologous PBMC loaded with graded amounts of tyrosinase peptide ($10^{-12}$ M-$10^{-5}$ M) and the tumor cell lines MaCa1, SK-Mel-28, Mel-A375, RCC-26, PancTu1, MaCa1/A2, UTS CC 1588, Mel-624.38, Mel-93.04A12, SK-Mel-23, SK-Mel-29 and WM-266-4 as stimulating cells at an E:T of 2:1.

REFERENCES

1. Liao, X., et al. Transfection of RNA encoding tumor antigens following maturation of dendritic cells leads to prolonged presentation of antigen and the generation of high-affinity tumor-reactive cytotoxic T lymphocytes. *Mol Ther* 9, 757-764 (2004).
2. Javorovic, M., et al. Inhibitory effect of RNA pool complexity on stimulatory capacity of RNA-pulsed dendritic cells. *J Immunother* 31, 52-62 (2008).
3. Altman, J. D., et al. Phenotypic analysis of antigen-specific T lymphocytes. *Science* 274, 94-96 (1996).

4. Ho, W. Y., Nguyen, H. N., Wolff, M., Kuball, J. & Greenberg, P. D. In vitro methods for generating CD8+ T-cell clones for immunotherapy from the naive repertoire. *J Immunol Methods* 310, 40-52 (2006).

5. Wolfel, T., et al. Analysis of antigens recognized on human melanoma cells by A2-restricted cytolytic T lymphocytes (CTL). *Int J Cancer* 55, 237-244 (1993).

6. Margulies, D. H. TCR avidity: it's not how strong you make it, it's how you make it strong. *Nat Immunol* 2, 669-670 (2001).

7. Palermo, B., et al. Qualitative difference between the cytotoxic T lymphocyte responses to melanocyte antigens in melanoma and vitiligo. *Eur J Immunol* 35, 3153-3162 (2005).

8. Engels, B., et al. Retroviral vectors for high-level transgene expression in T lymphocytes. *Hum Gene Ther* 14, 1155-1168 (2003).

9. Heemskerk, M. H., et al. Redirection of antileukemic reactivity of peripheral T lymphocytes using gene transfer of minor histocompatibility antigen HA-2-specific T-cell receptor complexes expressing a conserved alpha joining region. *Blood* 102, 3530-3540 (2003).

10. Rivoltini, L., et al. Quantitative correlation between HLA class I allele expression and recognition of melanoma cells by antigen-specific cytotoxic T lymphocytes. *Cancer Res* 55, 3149-3157 (1995).

11. Wolff, M., et al. Quantitation of MHC tetramer-positive cells from whole blood: evaluation of a single-platform, six-parameter flow cytometric method. *Cytometry A* 57, 120-130 (2004).

12. Zhou, D., et al. High throughput analysis of TCR-beta rearrangement and gene expression in single T cells. *Lab Invest* 86, 314-321 (2006).

13. Steinle, A., Reinhardt, C., Jantzer, P. & Schendel, D. J. In vivo expansion of HLA-B35 alloreactive T cells sharing homologous T cell receptors: evidence for maintenance of an oligoclonally dominated allospecificity by persistent stimulation with an autologous MHC/peptide complex. *J Exp Med* 181, 503-513 (1995).

14. Leisegang, M., et al. Enhanced functionality of T cell receptor-redirected T cells is defined by the transgene cassette. *J Mol Med* 86, 573-583 (2008).

15. Kieback, E., Charo, J., Sommermeyer, D., Blankenstein, T. & Uckert, W. A safeguard eliminates T cell receptor gene-modified autoreactive T cells after adoptive transfer. *Proc Natl Acad Sci USA* 105, 623-628 (2008).

16. Kolb, H. J., Schattenberg, A., Goldman, J. M., Hertenstein, B., Jacobsen, H., Arcese W., Ljungman, P., Ferrant, A., Verdonck, L. Niederwieser, B. et al. 1995. Graft-versus-leukemia effect of donor lymphocyte transfusions in marrow grafted patients. *Blood* 86:2041.

17. Kolb, H. J., Schmid, C., Barrett, A. J. and Schendel, D. J. (2004). Graft-versus-leukemia reactions in allogeneic chimeras. *Blood* 103:767-776.

18. Dudley, M. E. and Rosenberg, S. A. (2003). Adoptive-cell-transfer therapy for the treatment of patients with cancer. *Nature Reviews Cancer* 3: 666-675.

19. Dudley, M. E., Wunderlich, J. R., Robbins, P. F., Yang, J. C., Hwu, P., Schwartzentruber, D. J., Topalian, S. L., Sherry, R., Restifo, N. P., Hubicki, A. M., Robinson, M. R., Raffeld, M., Duray, P., Seipp, C. A., Rogers-Freezer, L., Morton, K. E., Mavroukakis, S. A., White, D. E., Rosenberg, S. A. (2002). Cancer regression and autoimmunity in patients after clonal repopulation with antitumor lymphocytes. *Science* 298:850-854.

20. Engels, B., Nossner, E., Frankenberger, B., Blankenstein, Th., Schendel, D. J., and W. Uckert. 2005. Redirecting human T lymphocytes towards renal cell carcinoma-specificity by retroviral transfer of T cell receptor genes. *Human Gene Ther.*, 16(7):79.9-810

21. Rivoltini L, Barracchini K C, Viggiano V, et al. Quantitative correlation between HLA class I allele expression and recognition of melanoma cells by antigen-specific cytotoxic T lymphocytes. *Cancer Res.* 1995; 55:3149-3157.

22. Schendel D J, Gansbacher B, Oberneder R, et al. Tumor-specific lysis of human renal cell carcinomas by tumor-infiltrating lymphocytes. I. HLA-A2-restricted recognition of autologous and allogeneic tumor lines. *J Immunol.* 1993; 151:4209-4220.

23. Steinle A, Reinhardt C, Jantzer P, Schendel D J. In vivo expansion of HLA-B35 alloreactive T cells sharing homologous T cell receptors: evidence for maintenance of an oligoclonally dominated allospecificity by persistent stimulation with an autologous MHC/peptide complex. *J Exp Med.* 1995; 181:503-513.

24. Cohen C J, Zhao Y, Zheng Z, Rosenberg S A, Morgan R A. Enhanced antitumor activity of murine-human hybrid T-cell receptor (TCR) in human lymphocytes is associated with improved pairing and TCR/CD3 stability. *Cancer Res.* 2006; 66:8878-8886.

25. Leisegang M, Engels B, Meyerhuber P, et al. Enhanced functionality of T cell receptor-redirected T cells is defined by the transgene cassette. *J Mol Med.* 2008; 86:573-583.

26. Scholten K B, Kramer D, Kueter E W, et al. Codon modification of T cell receptors allows enhanced functional expression in transgenic human T cells. *Clin Immunol.* 2006; 119:135-145.

What is claimed is:

1. A T cell expressing a T cell receptor (TCR), wherein the TCR binds to a tyrosinase peptide comprising the amino acid sequence of YMDGTMSQV (SEQ ID NO: 9) and is encoded by a nucleic acid comprising the nucleic acid sequence of SEQ ID NO: 7 coding for the α-chain and the nucleic acid sequence of SEQ ID NO: 8 coding for the β-chain of the TCR, or a derivative thereof, coding for the α- and β-chain, wherein the α- or β-chain has been altered by one or more additions or deletions of from 1-15 amino acids, the additions or deletions being outside the CDR3 region of each chain and/or by conservative substitutions of from 1-15 amino acids, the conservative substitutions being outside the CDR3 region of each chain.

2. The T cell of claim 1, wherein the TCR comprises the amino acid sequences of SEQ ID NO: 5 and/or SEQ ID NO: 6.

3. The T cell of claim 1, wherein the T cell is a peripheral blood lymphocyte (PBL).

4. A pharmaceutical composition comprising the TCR of claim 1 and a pharmaceutically acceptable carrier.

5. The pharmaceutical composition of claim 4, wherein the pharmaceutical composition is formulated as an infusion or injection.

6. The T cell of claim 1, wherein the TCR is encoded by a nucleic acid comprising the nucleic acid sequence of SEQ ID NO: 7 coding for the α-chain and the nucleic acid sequence of SEQ ID NO: 8 coding for the β-chain of the TCR.

* * * * *

SEQUENCE LISTING

<160> NUMBER OF SEQ ID NOS: 10

<210> SEQ ID NO 1
<211> LENGTH: 813
<212> TYPE: DNA
<213> ORGANISM: Artificial Sequence
<220> FEATURE:
<223> OTHER INFORMATION: TCR alpha chain sequence

<400> SEQUENCE: 1

```
atgtggggag ttttccttct ttatgtttcc atgaagatgg gaggcactac aggacaaaac      60
attgaccagc ccactgagat gacagctacg gaaggtgcca ttgtccagat caactgcacg     120
taccagacat ctgggttcaa cgggctgttc tggtaccagc aacatgctgg cgaagcaccc     180
```

```
acatttctgt cttacaatgt tctggatggt ttggaggaga aaggtcgttt ttcttcattc    240
cttagtcggt ctaaagggta cagttacctc cttttgaagg agctccagat gaaagactct    300
gcctcttacc tctgtgctgt gacatactct ggggctggga gttaccaact cactttcggg    360
aaggggacca aactctcggt cataccaaat atccagaacc ctgaccctgc cgtgtaccag    420
ctgagagact ctaaatccag tgacaagtct gtctgcctat tcaccgattt tgattctcaa    480
acaaatgtgt cacaaagtaa ggattctgat gtgtatatca cagacaaaac tgtgctagac    540
atgaggtcta tggacttcaa gagcaacagt gctgtggcct ggagcaacaa atctgacttt    600
gcatgtgcaa acgccttcaa caacagcatt attccagaag acaccttctt ccccagccca    660
gaaagttcct gtgatgtcaa gctggtcgag aaaagctttg aaacagatac gaacctaaac    720
tttcaaaacc tgtcagtgat tgggttccga atcctcctcc tgaaagtggc cgggtttaat    780
ctgctcatga cgctgcggct gtggtccagc tga                                 813

<210> SEQ ID NO 2
<211> LENGTH: 960
<212> TYPE: DNA
<213> ORGANISM: Artificial Sequence
<220> FEATURE:
<223> OTHER INFORMATION: TCR beta chain sequence

<400> SEQUENCE: 2
atgcttagtc ctgacctgcc tgactctgcc tggaacacca ggctcctctg ccatgtcatg     60
ctttgtctcc tgggagcagg ttcagtggct gctggagtca tccagtcccc aagacatctg    120
atcaaagaaa agagggaaac agccactctg aaatgctatc ctatccctag acacgacact    180
gtctactggt accagcaggg tccaggtcag gaccccagt tcctcatttc gttttatgaa    240
aagatgcaga gcgataaagg aagcatccct gatcgattct cagctcaaca gttcagtgac    300
tatcattctg aactgaacat gagctccttg gagctggggg actcagccct gtacttctgt    360
gccagcagtc agaaacaggg ctgggaaaaa ctgtttttt gcagtggaac ccagctctct    420
gtcttggagg acctgaacaa ggtgttccca cccgaggtcg ctgtgtttga gccatcagaa    480
gcagagatct cccacaccca aaaggccaca ctggtgtgcc tggccacagg cttcttccct    540
gaccacgtgg agctgagctg gtgggtgaat gggaaggagg tgcacagtgg ggtcagcacg    600
gacccgcagc ccctcaagga gcagcccgcc ctcaatgact ccagatactg cctgagcagc    660
cgcctgaggg tctcggccac cttctggcag aaccccgca accacttccg ctgtcaagtc    720
cagttctacg gcctctcgga gaatgacgag tggacccagg atagggccaa acccgtcacc    780
cagatcgtca gcgccgaggc ctggggtaga gcagactgtg ctttacctc ggtgtcctac    840 cagcaagggg tcctgtctgc caccatcctc tatgagatcc tgctagggaa ggccaccctg    900
tatgctgtgc tggtcagcgc ccttgtgttg atggccatgg tcaagagaaa ggatttctga    960

<210> SEQ ID NO 3
<211> LENGTH: 39
<212> TYPE: DNA
<213> ORGANISM: Artificial Sequence
<220> FEATURE:
<223> OTHER INFORMATION: Nucleotide sequence of CDR3 in TCR alpha chain

<400> SEQUENCE: 3
tgtgctgtga catactctgg ggctgggagt taccaactc                            39

<210> SEQ ID NO 4
```

```
<211> LENGTH: 36
<212> TYPE: DNA
<213> ORGANISM: Artificial Sequence
<220> FEATURE:
<223> OTHER INFORMATION: Nucleotide sequence of CDR3 in TCR beta chain

<400> SEQUENCE: 4
tgtgccagca gtcagaaaca gggctgggaa aaactg                               36

<210> SEQ ID NO 5
<211> LENGTH: 13
<212> TYPE: PRT
<213> ORGANISM: Artificial Sequence
<220> FEATURE:
<223> OTHER INFORMATION: Amino acid sequence of CDR3 in TCR alpha chain

<400> SEQUENCE: 5

Cys Ala Val Thr Tyr Ser Gly Ala Gly Ser Tyr Gln Leu
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Amino acid sequence of CDR3 in TCR beta chain

<400> SEQUENCE: 6

Cys Ala Ser Ser Gln Lys Gln Gly Trp Glu Lys Leu
1               5                   10

<210> SEQ ID NO 7
<211> LENGTH: 381
<212> TYPE: DNA
<213> ORGANISM: Artificial Sequence
<220> FEATURE:
<223> OTHER INFORMATION: Codon optimized VJ region of TCR alpha chain

<400> SEQUENCE: 7
atgtggggcg tgtttctgct gtacgtgtcc atgaagatgg gcggcaccac cggccagaac    60
atcgaccagc ccaccgagat gacagccacc gagggcgcca tcgtgcagat caactgcacc   120
taccagacca gcggcttcaa cggcctgttc tggtatcagc agcacgccgg cgaggcccct   180
accttcctga gctacaacgt gctggacggc ctggaagaga agggccggtt cagcagcttc   240
ctgagccggt ccaagggcta cagctacctg ctgctgaaag aactgcagat gaaggacagc   300
gccagctacc tgtgcgccgt gacctacagc ggagccggca gctaccagct gaccttcggc   360
aagggcacca agctgtccgt g                                             381

<210> SEQ ID NO 8
<211> LENGTH: 426
<212> TYPE: DNA
<213> ORGANISM: Artificial Sequence
<220> FEATURE:
<223> OTHER INFORMATION: Codon optimized VDJ region of TCR beta chain

<400> SEQUENCE: 8
atgctgtccc ccgatctgcc cgacagcgcc tggaacacca gactgctgtg ccacgtgatg    60
ctgtgtctgc tgggagccgg atctgtggcc gctggcgtga tccagagccc agacacctg   120 atcaaagaga gcgggagac agccacccctg aagtgctacc ccatcccccg gcacgacacc   180
gtgtactggt atcagcaggg accaggacag gaccccagt tcctgatcag cttctacgag   240
aagatgcaga gcgacaaggg cagcatcccc gacagattca gcgcccagca gttcagcgac   300
```

```
taccacagcg agctgaacat gagcagcctg gaactgggcg actctgccct gtacttctgc    360
gccagcagcc agaagcaggg ctgggagaag ctgttcttcg gcagcggcac ccagctgtcc    420
gtgctg                                                               426
```

<210> SEQ ID NO 9
<211> LENGTH: 9
<212> TYPE: PRT
<213> ORGANISM: Artificial Sequence
<220> FEATURE:
<223> OTHER INFORMATION: synthetic tyrosinase peptide

<400> SEQUENCE: 9

Tyr Met Asp Gly Thr Met Ser Gln Val
1               5

<210> SEQ ID NO 10
<211> LENGTH: 8
<212> TYPE: PRT
<213> ORGANISM: Artificial Sequence
<220> FEATURE:
<223> OTHER INFORMATION: synthetic influenza matrix protein

<400> SEQUENCE: 10

Gly Ile Leu Gly Phe Val Thr Leu
1               5